United States Patent
Holtan et al.

(10) Patent No.: US 12,391,851 B2
(45) Date of Patent: Aug. 19, 2025

(54) ADHESIVE COMPOSITIONS COMPRISING A COMBINATION OF (I) MICROFIBRILLATED CELLULOSE AND (II) A METAL IN AN OXIDATION STATE OF II OR GREATER

(71) Applicant: Borregaard AS, Sarpsborg (NO)

(72) Inventors: Synnøve Holtan, Sarpsborg (NO); Katérina Liapis, Sarpsborg (NO); Steen Jacobsen, Sarpsborg (NO); Hans Henrik Øvrebø, Sarpsborg (NO); Jan Berg, Sarpsborg (NO)

(73) Assignee: Borregaard AS, Sarpsborg (NO)

( * ) Notice: Subject to any disclaimer, the term of this patent is extended or adjusted under 35 U.S.C. 154(b) by 195 days.

(21) Appl. No.: 17/790,889

(22) PCT Filed: Feb. 5, 2021

(86) PCT No.: PCT/EP2021/052758
§ 371 (c)(1),
(2) Date: Jul. 5, 2022

(87) PCT Pub. No.: WO2021/156413
PCT Pub. Date: Aug. 12, 2021

(65) Prior Publication Data
US 2023/0051816 A1    Feb. 16, 2023

(30) Foreign Application Priority Data
Feb. 7, 2020    (EP) .................................... 20156214

(51) Int. Cl.
*A23L 29/212*    (2016.01)
*A23L 29/00*    (2016.01)
(Continued)

(52) U.S. Cl.
CPC .......... *C09J 101/02* (2013.01); *A23L 29/015* (2016.08); *A23L 29/212* (2016.08); *A23L 29/262* (2016.08);
(Continued)

(58) Field of Classification Search
CPC ........ B31F 1/2809; B31F 1/2818; B31F 5/04; B32B 3/28; B32B 7/12; B32B 29/002;
(Continued)

(56) References Cited

U.S. PATENT DOCUMENTS

2012/0289628 A1\* 11/2012 Ceulemans ............. C08L 33/02
524/48
2015/0233058 A1    8/2015 Neumann
2018/0163098 A1\*  6/2018 Dijk-van Delden ...... B32B 7/12

FOREIGN PATENT DOCUMENTS

EP       2599823 A1    6/2013
JP    2004002656 A    1/2004
(Continued)

OTHER PUBLICATIONS

International Search Report for PCT/EP2021/052758, filed Feb. 5, 2021, 4 pages, (mailed May 26, 2021).
(Continued)

*Primary Examiner* — Michael A Tolin
(74) *Attorney, Agent, or Firm* — Choate, Hall & Stewart LLP; Michael D. Schmitt

(57) ABSTRACT

The present invention relates to an adhesive composition comprising, among others, (i) microfibrillated cellulose and (ii) a metal in oxidation state of II or greater. The present invention further relates to uses of such an adhesive composition and to products prepared with such an adhesive composition. Furthermore, the present invention relates to a
(Continued)

process for making corrugated paperboards or cardboards, or solid paperboards or cardboards by using such an adhesive composition.

23 Claims, 8 Drawing Sheets

(51) Int. Cl.

| | |
|---|---|
| A23L 29/262 | (2016.01) |
| A23L 29/269 | (2016.01) |
| A61L 15/60 | (2006.01) |
| B31F 1/28 | (2006.01) |
| B31F 5/04 | (2006.01) |
| B32B 29/08 | (2006.01) |
| C03C 25/321 | (2018.01) |
| C03C 25/46 | (2006.01) |
| C09D 7/61 | (2018.01) |
| C09D 101/02 | (2006.01) |
| C09D 103/02 | (2006.01) |
| C09D 103/04 | (2006.01) |
| C09J 11/04 | (2006.01) |
| C09J 101/02 | (2006.01) |
| C09J 103/02 | (2006.01) |
| C09J 103/04 | (2006.01) |

(52) U.S. Cl.
CPC ............ *A23L 29/273* (2016.08); *A61L 15/60* (2013.01); *B31F 1/2809* (2013.01); *B31F 5/04* (2013.01); *C03C 25/321* (2013.01); *C03C 25/46* (2013.01); *C09D 7/61* (2018.01); *C09D 101/02* (2013.01); *C09D 103/02* (2013.01); *C09D 103/04* (2013.01); *C09J 11/04* (2013.01); *C09J 103/02* (2013.01); *C09J 103/04* (2013.01); *C09J 2401/00* (2013.01); *C09J 2403/00* (2013.01)

(58) Field of Classification Search
CPC ....... B32B 29/005; B32B 29/06; B32B 29/08; B32B 2250/26; C08B 31/003; C08B 31/006; C08K 3/22; C08K 3/26; C08K 3/30; C08K 2003/2227; C08K 2003/3045; C08K 2003/3081; C08L 1/02; C09J 5/06; C09J 11/04; C09J 101/00; C09J 101/02; C09J 103/00; C09J 103/02; C09J 103/04; C09J 103/06; C09J 103/08; C09J 103/10; C09J 129/04; C09J 2400/283; C09J 2401/00; C09J 2401/006; C09J 2403/00; D21H 11/18; D21H 17/25; D21H 17/28; D21H 17/36; D21H 17/37; D21H 21/16; D21H 27/40; A23L 29/015; A23L 29/212; A23L 29/219; A23L 29/262; A23L 29/269; A23L 29/273; A61L 15/60; C03C 25/321; C03C 25/46; C09D 7/61; C09D 101/00; C09D 101/02; C09D 103/00; C09D 103/02; C09D 103/04; C09D 103/06; C09D 103/08; C09D 103/10
See application file for complete search history.

(56) References Cited

FOREIGN PATENT DOCUMENTS

| | | |
|---|---|---|
| WO | WO-97/15440 A1 | 5/1997 |
| WO | WO-2007/091942 A1 | 8/2007 |
| WO | WO-2015/180844 A1 | 12/2015 |
| WO | WO-2018/083590 A1 | 5/2018 |
| WO | WO-2020/008023 A1 | 1/2020 |

OTHER PUBLICATIONS

Written Opinion for PCT/EP2021/052758, filed Feb. 5, 2021, 7 pages, (mailed May 26, 2021).

\* cited by examiner

FIG: 5
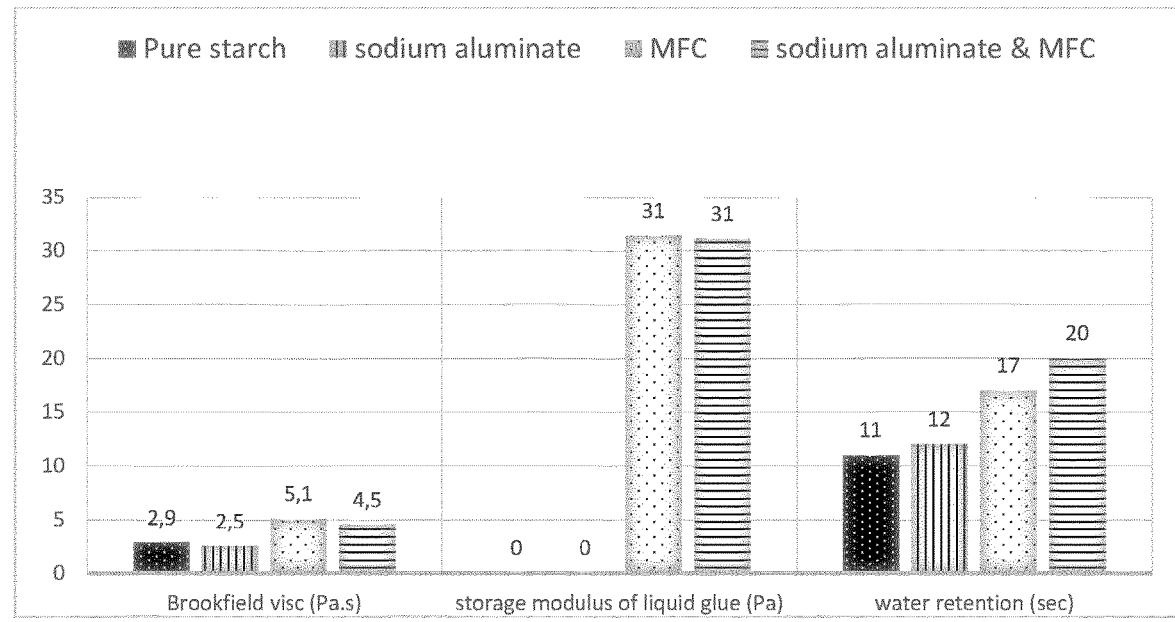
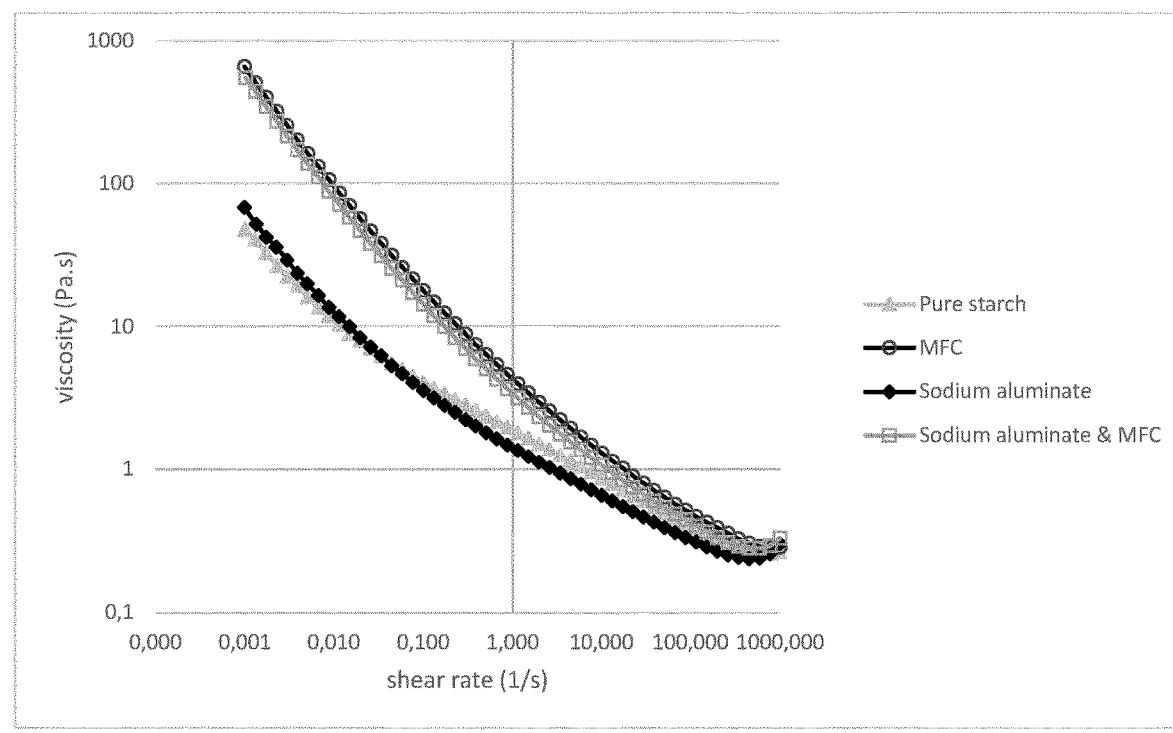

ADHESIVE COMPOSITIONS COMPRISING A COMBINATION OF (I) MICROFIBRILLATED CELLULOSE AND (II) A METAL IN AN OXIDATION STATE OF II OR GREATER

FIELD OF THE INVENTION

The present invention relates to an adhesive composition comprising, in conjunction and at least, (i) microfibrillated cellulose (MFC) and (ii) a metal in an oxidation state of II or greater. The present invention further relates to uses of such an adhesive composition and to products prepared with such an adhesive composition. Furthermore, the present invention relates to a process for making corrugated boards or solid boards by using such an adhesive composition.

BACKGROUND OF THE INVENTION

Compositions that comprise at least one solvent, e.g. water, and at least one compound that (a) is capable of polymerizing, or has already partly or fully polymerized, and that (b) has at least two groups available for hydrogen bonding, preferably OH groups (in the following also referred to as "compound capable of polymerizing and hydrogen bonding"), are of practical relevance in a variety of applications, in which the composition is meant to at least partially cure after application onto a substrate. Examples for such applications, without being limited thereto are adhesive coatings, protective coatings, primer coatings, surface sizing coatings etc.

As examples of such compounds capable of polymerizing and hydrogen bonding, starch- and PVA (polyvinyl alcohol)-based adhesive compositions are advantageously used in the packaging industry, e.g. for manufacturing corrugated boards or solid boards, respectively.

In such adhesive compositions, a cross-linker is commonly used to improve curing and bonding between the molecules of the composition and with the substrate.

Boron-containing compounds such as borax and boric acid are/were frequently used as cross-linkers. However, such cross-linkers commonly have at least one, or any combination (including all), of the following drawback(s):
 increased or undesirable levels of toxicity
 other potentially hazardous (chemical) properties
 negative impact on the environment
 no or only limited biodegradability.

In spite of these concerns, borax was or still is regarded as an indispensable additive for adhesives and various industrial applications. However, not only due to its addition to the Candidate List of Substances of Very High Concern (SVHC) as CMR substances by the European Chemicals Agency (ECHA) in 2011, borax has become a controversial raw material that the cardboard industry generally strives to replace. Replacing borax by other, harmless materials, however, is not straightforward and one of the major challenges that the cardboard manufacturing industry is currently facing.

In production processes for corrugated boards, a bottleneck commonly encountered is the ability to efficiently glue together flute and liner (see FIG. 7), in particular in complex and heavy paper qualities, typically at the double-backer glue station or at the inlet of the heating section. It has been found that, for the heaviest and most complex qualities of corrugated boards, the glue-ability and/or the speed of gelatinization upon heating may require further improvement if borax is to be (fully) replaced by MFC. In some instances, either the boards delaminate, or the corrugator must be run at lower speed to gain more heat and overcome this specific shortcoming. Therefore, combinations of MFC and (some) borax are still seen as generally advantageous to enable high running speed when producing these demanding qualities.

MFC may also advantageously be used to replace boric acid in other adhesive applications, namely in PVA-based adhesive compositions. While certain improved properties are achieved by replacing boric acid with MFC, PVA-based adhesive compositions still are seen as suffering from an unsatisfactory low tack in some application areas, in particular in solid boards production if boric acid is (fully) replaced.

Several strategies for replacing boron-containing cross-linkers, in particular borax, in adhesive compositions have been developed over the last years. In one strategy, microfibrillated cellulose is used as a full or partial substitute for borax, in particular in starch-based adhesive compositions (WO 2019/034649).

Another approach known from the art (for example from WO 2013/087530) for avoiding boron-containing cross-linkers, in particular borax, in adhesive compositions is the use of sodium aluminate, in particular for replacing borax in starch-based adhesive compositions. In alkaline aqueous media, aluminate is believed to form $Al(OH)_4^-$ ions, which are believed to act as a crosslinker for the starch polymers according to the following general reaction mechanism:

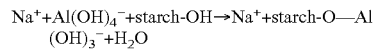

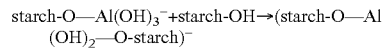

However, simply replacing all or most of the borax or boric acid by aluminate does not result in acceptable adhesive compositions.

Without wishing to be bound by theory, it is believed that these glues are not stable enough to allow for running the corrugator at high speed, not least because the rheology (viscosity) and elastic properties of such glues are not sufficient for demanding applications. Also, high water uptake of adhesives known from the art may be detrimental to the quality of the end product.

Thus, boron-free, in particular borax- and boric acid-free adhesive compositions are still highly sought-after for a variety of applications, in particular for manufacturing corrugated (card)boards and solid boards.

SUMMARY OF THE PRESENT INVENTION

Based on the above, it is an object of the present invention to provide boron-free, in particular borax- and boric acid-free, adhesive compositions that avoid or minimize the drawbacks of compositions known from the art as discussed above. In particular, glue stability, rheology, initial tack and adhesion properties as well as processing speed on a corrugated board production line are to be improved.

These and other objects is/are achieved by means of using a unique combination of (i) microfibrillated cellulose (MFC) and (ii) a metal in an oxidation state of II or greater as a full or partial substitute for boron-containing crosslinkers, in particular borax and boric acid.

In accordance with the present invention, a metal in an oxidation state of II or higher refers to any metal as commonly understood by the skilled person that is stable in at least one oxidation state of II or higher. For example, alkaline metals are not included, since these commonly are stable only in an oxidation state of I.

As one of skill in the art knows, various metals are stable in more than one oxidation state.

Such metals are also referred to as polyvalent metals. For example, Aluminum has three stable oxidation states. The most common oxidation state is III (+3). The other two are I (+1) and II (+2). Aluminum in the oxidation state I is not in accordance with the present invention, while Aluminum in the oxidation states II and III is.

In accordance with the present invention, the term oxidation state is to be understood to be in accordance with *IUPAC. Compendium of Chemical Terminology, 2nd ed. (the "Gold Book")*. Compiled by A. D. McNaught and A. Wilkinson. Blackwell Scientific Publications, Oxford (1997). Online version (2019) created by S. J. Chalk. ISBN 0-9678550-9-8. https://doi.org/10.1351/goldbook.

The metal in an oxidation state of II or greater can be present in the composition as a monoatomic ion (i.e. an ion consisting of exactly one atom), in the form of a polyatomic ion (i.e. an ion composed of two or more covalently bonded atoms or of a metal complex), in the form of a salt, as part of a polymeric network, or any combination thereof. For example, the polyatomic ion may be a hydrate or an hydroxide, or an oxide hydroxide or any mixture thereof.

In embodiments of the invention said metal in an oxidation state of II or higher comprises a metal selected from group 2 of the periodic system of elements (PSE), in particular Mg or Ca, or from group 4, in particular Ti, Zr or Hf, or from group 8, in particular Fe, or from group 12, in particular Zn, or from group 13, in particular Al.

In embodiments of the invention said metal in an oxidation state of II or higher comprises a metal, in particular an ion, selected from the group of Aluminum, Calcium, Zirconium, Magnesium, Zink, Hafnium or Titanium, or any combination thereof, preferably comprises an ion of Aluminum.

In accordance with the present invention, whenever reference is made to an "ion", monoatomic ions (which may also be denoted as "naked" ions, e.g. $Al^{3+}$) as well as polyatomic ions (e.g. a complex ion with coordinated ligands [e.g. $Al(OH)_4^-$]) are included.

The present invention is at least partly based on the realization that a relatively small amount of the metal in an oxidation state of II or higher (relative to the amount of the "compound capable of polymerizing and hydrogen bonding" and relative to the overall composition) is required to achieve the advantageous effects underlying the present invention, in particular high processing speeds in gluing together/laminating boards, in particular paper boards/cardboards. Indeed, a very small amount of said metal in an oxidation state of II or higher relative to the overall amount of composition is required.

Together with the fact that MFC as used as the primary adjuvant to improve the adhesive properties of the overall adhesive (and to make the use of boron-containing compounds obsolete) is an entirely natural product, overall, a highly sustainable and environmentally compatible adhesive can be provided in accordance with the present invention.

Therefore, in accordance with the present invention, the relative amount (concentration) of the metal in an oxidation state of II or higher complies with at least one of the following:

(i) the amount of moles of the metal in an oxidation state of II or higher relative to the weight, in kg, of the overall adhesive composition, including solvent, is from 0.0005 to 5, preferably from 0.001 to 1, further preferably from 0.005 to 0.5, further preferably from 0.01 to 0.2, further preferably from 0.02 to 0.1;

(ii) the amount of moles of the metal in an oxidation state of II or higher, relative to the weight of the dry mass of the at least one compound that is capable of polymerizing and hydrogen bonding, in kg, is from 0.002 to 20, preferably 0.05 to 5, preferably from 0.08 to 2, further preferably from 0.1 to 1.5 or (iii) the metal in an oxidation state of II or higher is present as an oxide, hydroxide or oxyhydroxide, or any mixture thereof, and the weight percentage of said oxide, hydroxide or oxyhydroxide relative to the weight of the overall composition, including solvent, is from 0.001 to 3, preferably from 0.05 to 2, even more preferably from 0.06 to 1.5, even more preferably from 0.1 to 1, even more preferably from 0.1 to 0.4.

In accordance with a first aspect of the present invention, this object and others is/are achieved by an adhesive composition as defined in claim 1.

In accordance with a second aspect of the present invention, this object and others is/are achieved by the use of the inventive adhesive composition for the preparation of corrugated boards or solid boards.

In accordance with a third aspect of the present invention, this object and others is/are achieved by the use of a combination of (i) MFC and (ii) a metal in an oxidation state of II or higher for preparing an adhesive composition.

In accordance with a fourth aspect of the present invention, this object and others is/are achieved by a corrugated board and a solid board as defined in the claims.

In accordance with a fifth aspect of the present invention, this object and others is/are achieved by a process for making corrugated boards as defined in the claims.

BRIEF DESCRIPTION OF THE FIGURES

FIG. 3: compositions 15, 14, 11, 16 as described in the "Examples" Section).

FIG. 5 (upper panel) shows Brookfield viscosity, storage modulus and water retention for adhesive compositions based on starch only, starch plus MFC, starch plus metal ion (all comparative) and starch plus MFC and metal ion (in accordance with the present invention); the lower panel shows the viscosity as function of the shear rate for the same compositions.

DETAILED DESCRIPTION OF THE INVENTION

This invention is at least partly based on the surprising finding that boron-containing cross-linkers as used in adhesive compositions, in particular borax and boric acid, can be fully replaced by a combination of MFC and a metal ion in an oxidation state of II or greater.

For example, it has been shown that aluminum sulfate and sodium aluminate, which form, depending on the pH, $Al^{3+}$ or a polyatomic aluminum-containing ion (e.g. $Al(OH)_4^-$) in situ are particularly advantageous for preparing the adhesive composition.

As one of skill in the art knows, the species in which aluminum ions are present in aqueous media depends on the pH. It is generally understood that the predominant aluminum species at high pH is the aluminate ion $Al(OH)_4^-$, whereas at low pH, $Al^{3+}$ is dominating. Other relevant species include, among others, $Al(OH)_3$, $Al(OH)_2^+$, $Al_2(OH)_2^{4+}$. Moreover, the kind of aluminum species present will also depend on the temperature and the concentration. For example high concentrations at high pH may lead to condensation reactions to form $Al_2O(OH)_5^{2-}$.

Figure 8:
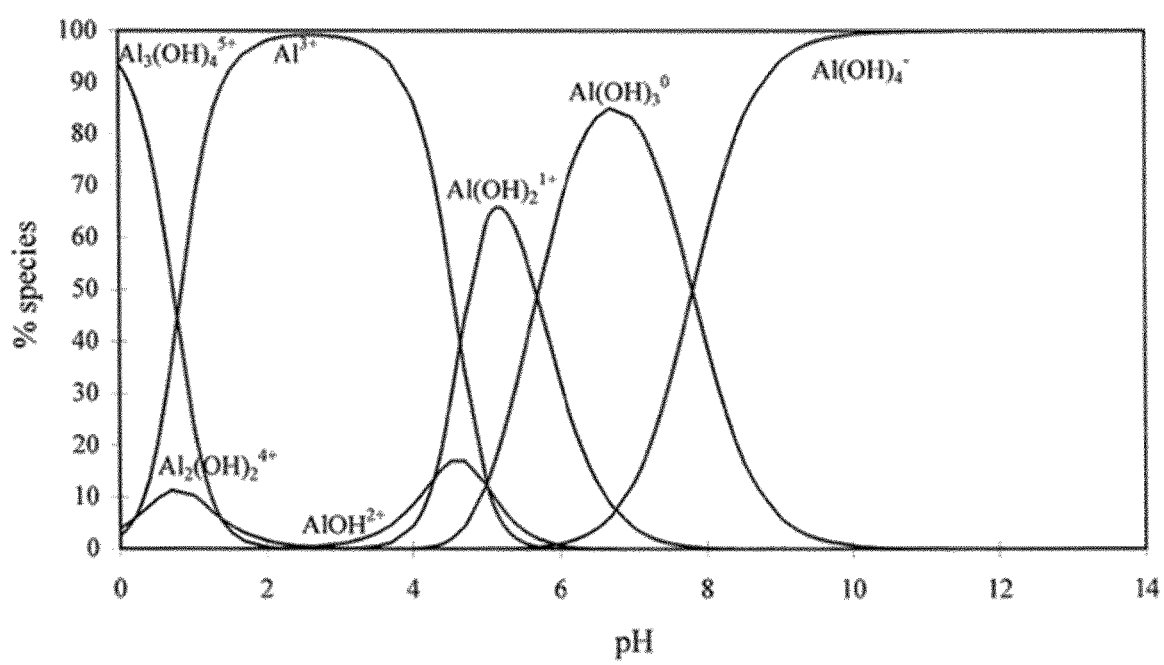
FIG. 8 shows aluminum species as they are typically present in aqueous media, depending on the pH.

An exemplary overview of the different aluminum species relative to the pH is shown in FIG. 8.

In the present invention, it has surprisingly been found that an adhesive composition in which boron-containing cross-linkers, in particular borax and boric acid, have been fully replaced by a combination of MFC and a metal in an oxidation state of II or greater shows improved initial tack and adhesion properties, as well as higher processing speeds on a corrugated board production line.

Specifically, it has been found that a combination of MFC and a metal in an oxidation state of II or greater achieves adhesive effects that are greater than the sum of the effects of the individual compounds, i.e. MFC, on the one hand, and said metal in oxidation state of II or greater as borax replacements, on the other hand.

Thus, surprisingly, it has been found that a combination of MFC and a metal in an oxidation state of II or greater leads to a synergistic effect, i.e. improved bonding strength and processability above and beyond the bonding strength and processability that is obtained when using MFC alone or a metal ion in an oxidation state of II or greater alone.

In accordance with the present invention, an "adhesive", "adhesive composition", or the like, is understood to be a material that is applied to substrates, e.g. the surfaces of articles to join these surfaces permanently by an adhesive bonding process. An adhesive is a substance capable of forming bonds to each of the two parts, wherein the final object consists of two sections (substrates) that are bonded together. A particular feature of adhesives is the fact that only comparatively small quantities that are required for bonding compared to the weight of the final object.

In accordance with the present invention, although "borax" and boric acid are generally understood to not be the same compound; [borax is a salt of boric acid, i.e. borax is sodium (tetra)borate, while boric acid is hydrogen borate], whenever the term "borax" is used, the term refers to boric acid and its alkaline metal salts. In particular, a number of related minerals or chemical compounds that differ primarily in their crystal water content are referred to as "borax" and are included within the scope of the present invention, in particular the decahydrate. Commercially sold borax is typically partially dehydrated. In accordance with the present invention the term "borax" also encompasses boric acid or borax derivatives, e.g. boric acid or borax that has been chemically or physically modified.

Unless explicitly stated otherwise, all ranges or values given for the amount of any component in the compositions of the present invention are meant to be given in weight % of the component relative to the total weight of the adhesive composition ("wt./wt.").

In accordance with the present invention, a "starch" as the claimed at least one compound that is (a) capable of polymerizing or has already partly or fully polymerized, and that (b) has at least two groups available for hydrogen bonding that are capable of crosslinking with at least one functional group of the microfibrillated cellulose and/or the at least one metal in an oxidation state of II or higher, is a polymeric carbohydrate comprising a plurality of glycosidic bonds.

Preferred sources of starch are corn, wheat, pea, potatoes, rice, tapioca and sago, among others.

In accordance with the present invention, a modified starch is a starch that has been chemically modified, for example by hydrolysis.

In embodiments of the present invention, the starch preferably is unmodified wheat starch or corn starch, but can be any of the starches commonly used in an adhesive, that is, all starches and derivatives, which contain sufficient available hydroxyl groups so that a copolymerization reaction can occur between them and other reactants.

In accordance with the present invention, a polyvinyl alcohol (PVA) as the least one compound that is (a) capable of polymerizing or has already partly or fully polymerized, and that (b) has at least two groups available for hydrogen bonding that are capable of crosslinking with at least one functional group of the microfibrillated cellulose refers to a water-soluble synthetic polymer having the formula/repeating unit —$[CH_2CH(OH)]_n$—.

Microfibrillated cellulose (also known as "reticulated" cellulose or as "superfine" cellulose, or as "cellulose nanofibrils", among others) is a cellulose-based product and is described, for example, in U.S. Pat. Nos. 4,481,077, 4,374,702 and 4,341,807. In accordance with the present invention, microfibrillated cellulose has at least one reduced length scale (diameter, fiber length) vis-à-vis non-fibrillated cellulose. In (non-fibrillated) cellulose, which is the starting product for producing microfibrillated cellulose (typically present as a "cellulose pulp"), no, or at least not a significant or not even a noticeable portion of individualized and "separated" cellulose "fibrils" can be found. The cellulose in wood fibres is an aggregation of fibrils. In cellulose (pulp), elementary fibrils are aggregated into microfibrils which are further aggregated into larger fibril bundles and finally into cellulosic fibres. The diameter of wood based fibres is typically in the range of 10-50 µm (with the length of these fibres being even greater). When the cellulose fibres are microfibrillated, a heterogeneous mixture of "released" fibrils with cross-sectional dimensions and lengths from nm to µm may result. Fibrils and bundles of fibrils may co-exist in the resulting microfibrillated cellulose. The diameter of the microbrillated cellulose of the present invention is typically in the nanometer range.

The microfibrillated cellulose may be prepared or obtained by a process, which comprises at least the following steps:

(a) subjecting a cellulose pulp to at least one mechanical pretreatment step; (b) subjecting the mechanically pretreated cellulose pulp of step (a) to a homogenizing step, which results in fibrils and fibril bundles of reduced length and diameter vis-à-vis the cellulose fibers present in the mechanically pretreated cellulose pulp of step (a), said step (b) resulting in microfibrillated cellulose; wherein the homogenizing step (b) involves compressing the cellulose pulp from step (a) and subjecting the cellulose pulp to a pressure drop.

The mechanical pretreatment step preferably is or comprises a refining step. The purpose of the mechanical pretreatment is to "beat" the cellulose pulp in order to increase the accessibility of the cell walls, i.e. to increase the surface area.

A refiner that is preferably used in the mechanical pretreatment step comprises at least one rotating disk. Therein, the cellulose pulp slurry is subjected to shear forces between the at least one rotating disk and at least one stationary disk. Prior to the mechanical pretreatment step, or in addition to the mechanical pretreatment step, enzymatic (pre)treatment of the cellulose pulp is an optional additional step that may be preferred for some applications. In regard to enzymatic pretreatment in conjunction with microfibrillating cellulose, the respective content of WO 2007/091942 is incorporated herein by reference. Any other type of pretreatment, including chemical pretreatment is also within the scope of the present invention.

In the homogenizing step (b), which is to be conducted after the (mechanical) pretreatment step, the cellulose pulp slurry from step (a) is passed through a homogenizer at least once, preferably at least two times, as described, for example, in PCT/EP2015/001103.

In the microfibrillated cellulose as described throughout the present disclosure, individual fibrils or fibril bundles can be identified and easily discerned by way of conventional optical microscopy, for example at a magnification of 40×, and/or by electron microscopy (SEM or TEM).

In embodiments, the microfibrillated cellulose in accordance with the present invention is characterized, among others, by at least one of the following features:

In embodiments of the present invention, the microfibrillated cellulose is characterized in that it results in gel-like dispersion that has a zero shear viscosity, no, of at least 2000 Pa·s, preferably of at least 3000 Pa·s or 4000 Pa·s, further preferably of at least 5000 Pa·s, further preferably at least 6000 Pa·s, further preferably at least 7000 Pa·s, as measured in polyethylene glycol (PEG) as the solvent, and at a solids content of the MFC of 0.65%, wherein the measurement method is as described in the description.

The zero shear viscosity, no ("viscosity at rest") is a measure for the stability of the three-dimensional network making up the gel-like dispersion.

The "zero shear viscosity" as disclosed and claimed herein is measured as described in the following. Specifically, the rheological characterization of the MFC dispersions ("comparative" and "in accordance with the invention") was performed with PEG 400 as the solvent. "PEG 400" is a polyethylene glycol with a molecular weight between 380 and 420 g/mol and is widely used in pharmaceutical applications and therefore commonly known and available.

The rheological properties, in particular zero shear viscosity was/were measured on a rheometer of the type Anton Paar Physica MCR 301. The temperature in all measurements was 25° C. and a "plate-plate" geometry was used (diameter: 50 mm). The rheological measurement was performed as an oscillating measurement (amplitude sweep at a frequency of 1 Hz) to evaluate the degree of structure in the dispersions and as rotational viscosity measurements, in which case the viscosity was measured as a function of the shear rate to evaluate the viscosity at rest (shear forces→0), as well as the shear thinning properties of the dispersions. The measurement method is further described in PCT/EP2015/001103 (EP 3 149 241).

In embodiments, the microfibrillated cellulose has a water holding capacity (water retention capacity) of more than 30, preferably more than 40, preferably more than 50, preferably more than 60, preferably more than 70, preferably more than 75, preferably more than 80, preferably more than 90, further preferably more than 100. The water holding capacity describes the ability of the MFC to retain water within the MFC structure and this again relates to the accessible surface area. The water holding capacity is measured by diluting the MFC samples to a 0.3% solids content in water and then centrifuging the samples at 1000 G for 15 minutes. The clear water phase was separated from the sediment and the sediment was weighed. The water holding capacity is given as (mV/mT)−1 where mV is the weight of the wet sediment and mT is the weight of dry MFC analyzed. The measurement method is further described in PCT/EP2015/001103 (EP 3 149 241).

In embodiments of the invention, the MFC has a Schopper-Riegler (SR) value as obtained in accordance with the standard as defined in EN ISO 5267-1 (in the version of 1999) of below 95, preferably below 90, or, in the alternative, cannot be reasonably measured in accordance with the Schopper-Riegler method, as the MFC fibers are so small that a large fraction of these fibers simply passes through the screen as defined in the SR method.

In embodiments of the invention, the microfibrillated cellulose is non-modified (native) microfibrillated cellulose, preferably non-modified microfibrillated cellulose derived from plant material.

The viscosity of the starch-based adhesives as described throughout the present application and, in particular, in the examples is determined as the "Lory viscosity" in units of "seconds" and determined by the following method. Lory viscosity is measured with a Lory viscosity cup (Elcometer model 2215/1), according to standards ASTM D 1084-D or ASTM D4212. The Elcometer device consists of a conventional cylindrical cup with a needle fixed to the bottom. The cup is first dipped into the adhesive, which then empties through an escape hole. The flow time is measured as soon as the point of the needle is discernible.

The determination of the shear viscosity of the adhesives was performed on a rheometer (Anton Paar Physica MCR 102). A concentric cylinder geometry was used. To determine the shear profile, a shear rate sweep from 0.001 1/s to 1000 1/s followed by a shear rate sweep from 1000 1/s to 0.001 1/s was performed et 25° C. The shear viscosity was measured as a function of the shear rate.

The determination of the storage modulus of the adhesives was performed on a rheometer (Anton Paar Physica, MCR 102). A concentric cylinder geometry was used. To determine the storage modulus, a strain rate sweep from 0.01 to 1000% at a constant frequency of 1 Hz and at 25° C. was performed. The storage modulus was determined as the average of the storage modulus values corresponding to the linear viscoelastic plateau. The gelatinization peak viscosity was measured by increasing the temperature.

Without wishing to be bound by theory, it is believed that the addition of microfibrillated cellulose to a composition comprising at least one compound that is (a) capable of polymerizing or has already partly or fully polymerized, and that (b) has at least two groups available for hydrogen bonding, preferably OH groups, that are capable of crosslinking with at least one functional group of the microfibrillated cellulose (for simplicity, this compound is also referred to herein as the "at least one compound") leads to a network structure based on physical and/or chemical interactions between the microfibrillated cellulose units and the at least one compound by way of hydrogen bonding.

It is believed that microfibrillated cellulose is an efficient thickener in polar, in particular protic, solvent systems, in particular in water, and builds large three dimensional networks of fibrils which are stabilized by hydrogen bonds.

The MFC fibrils have hydroxyl groups on the surface that are dissociated ($O^-$) at high pH, thus leading to intra and inter-particular interactions.

Starch is essentially composed of amylose and amylopectin. Amylose is a helical linear polymer composed of $\alpha(1\rightarrow 4)$-bound D-glucose units, with hydroxyl groups which are pointed towards outside the helix. The fibril network of microfibrillated cellulose is believed to interact through hydrogen bonding with those groups, building up a protective layer around the amylose chains, thus protecting the starch against high shear degradation and stabilizing the viscosity. Overall, MFC is a network of entangled fibrils that can entrap starch molecule and in that way strengthen the starch composition and improve adhesion properties. The same overall effect is achieved for PVA. It is further believed that these networks are further stabilized by the presence of (comparatively small amounts) of the metal in an oxidation state of II or higher, in accordance with the present invention.

Furthermore, without wishing to be bound by theory, the water holding capacity of microfibrillated cellulose is believed to prevent water from migrating to and through the paper. Therefore, adding microfibrillated cellulose to adhesives comprising the "at least one compound" is particularly useful for the manufacture of corrugated boards, where water migration out of the adhesive into the paper destabilizes the final corrugated board product and may lead to warp and delamination, among others. Above and beyond, this effect is also advantageous for the manufacture of other board structures such as solid boards.

Further and importantly, without wishing to be bound by theory, the observed decrease in water uptake upon addition of MFC is explained by the fact that the —OH groups of the "at least one compound", such as starch or PVA, which are available for water uptake will interact with the MFC instead and, thus, are no longer available for binding water.

Decreasing the water uptake of the adhesive is generally desirable since water uptake in the final product, for example around the edges, may lead to swelling and deformation, which is generally undesirable. Furthermore, MFC is providing barrier properties in the cured adhesives, which seals the edges of the boards improving the water resistance of the cured boards and final products.

According to a first embodiment, the present invention relates to an adhesive composition, comprising a) microfibrillated cellulose; b) a metal ion in an oxidation state of II or greater; c) at least one compound that is capable of polymerizing or has already partly or fully polymerized, and that has at least two groups available for hydrogen bonding, preferably OH groups, that are capable of crosslinking with at least one functional group of the microfibrillated cellulose and/or the at least one metal in an oxidation state of II or higher; and d) at least one solvent.

In embodiments of the invention, the adhesive composition is characterized in that the relative amount (concentration) of the metal in an oxidation state of II or higher complies with at least one of the following:

(i) the amount of moles of the metal in an oxidation state of II or higher, relative to the weight, in kg, of the overall adhesive composition, including solvent, is from 0.0005 to 5, preferably from 0.001 to 1, further preferably from 0.005 to 0.5, further preferably from 0.01 to 0.2, further preferably from 0.02 to 0.1;

(ii) the amount of moles of the metal in an oxidation state of II or higher, relative to the weight of the dry mass of the at least one compound that is capable of polymerizing and hydrogen bonding, in kg, is from 0.002 to 20, preferably from 0.05 to 5, further preferably from 0.08 to 2, further preferably from 0.1 to 1.5; or (iii) the metal in an oxidation state of II or higher is present as an oxide, hydroxide or oxyhydroxide, or any mixture thereof, and the weight percentage of said oxide, hydroxide or oxyhydroxide relative to the weight of the overall composition, including solvent, is from 0.001 to 3, preferably from 0.05 to 2, even more preferably from 0.06 to 1.5, even more preferably from 0.1 to 1, even more preferably from 0.1 to 0.4.

The amount (concentration) of the metal in an oxidation state of II or higher can be determined in different ways. For example, one can calculate the amount of the metal in an oxidation state of II or higher from the "metal ion source" that is used for preparing the adhesive composition.

For example, if 342.13 g of anhydrous aluminum sulfate ($Al_2(SO_4)_3$) are used for preparing 1 kg of adhesive composition, then the adhesive composition contains 2 mol aluminum in an oxidation state of II or higher per kg of adhesive composition. Alternatively, the amount of the metal in an oxidation state of II or higher may be determined directly from the adhesive composition by means of known analytical means. For example, atomic emission spectroscopy can be used for determining the amount of the metal in an oxidation state of II or higher in an adhesive composition. Further analytical methods that can be used for determining the amount of the metal in an oxidation state of II or higher in an adhesive composition are, e.g., atomic absorption spectroscopy, or ICP-MS.

The MFC can be selected from the MFCs as defined hereinabove and herein below.

The metal in an oxidation state of II or greater preferably comprises an Aluminum ion, further preferably $Al^{3+}$ or a polyatomic aluminum-containing ion. As noted above, the species in which aluminum ions are present in aqueous media depends on the pH, temperature, concentration and other components present. The skilled person knows which species are present at which pH (see, e.g., FIG. 8 as reproduced from Panias et al. (2001), Hydrometallurgy, Volume 59, issue 1, pages 15-29).

The metal ions of the present invention may also comprise any amount of crystal water coordinated, or the ions may be part of oxide/hydroxide mixtures.

The metal in an oxidation state of II or greater that is present in the inventive composition is generally derived from a "metal ion source". A "metal ion source", as used herein, refers to the compound that is used for introducing the metal in an oxidation state of II or greater into the composition. For example, aluminum sulfate and sodium aluminate are aluminum sources for introducing aluminum in an oxidation state of II or greater into the composition. As the skilled person knows, aluminum sulfate and sodium aluminate then form, depending on the pH, the monoatomic ion $Al^{3+}$ or polyatomic aluminum-containing ions, e.g. $Al(OH_4)^-$ (see FIG. 8).

Preferred metal ion sources are for example salts, oxides and the like, which comprise the metal in an oxidation state of II or greater.

Preferred sources for aluminum in an oxidation state of II or greater are liquid or solid forms of aluminum sulfate, sodium aluminate (e.g. liquid $Na_2Al_2O_4$ (aluminum sodium dioxide) or solid $NaAlO_2$ (aluminum sodium oxide), both with aluminum content calculated as % aluminum oxide), aluminum chloride, aluminum nitrate, aluminum silicate, polyaluminum chloride, ammonium aluminum sulfate, aluminum potassium sulfate, aluminum sodium sulfate, potassium aluminate, or even other aluminum derivatives and/or aluminum oxide, and/or aluminum hydroxide. Particularly preferred sources for aluminum in an oxidation state of II or greater are aluminum sulfate, sodium aluminate, and aluminum hydroxide.

Preferably, the aluminum ion or aluminum-containing ion is derived from sodium aluminate and/or aluminum sulfate $(Al_2(SO_4)_3)$.

Other preferred metals in an oxidation state of II or greater are Zirconium or Calcium.

Preferably, the metal ion source is present in an amount such that the adhesive composition comprises the at least one metal in an oxidation state of II or higher relative to the weight, in kg, of the overall adhesive composition, including solvent, in a concentration of from 0.0005 to 5 mol, preferably from 0.001 to 1 mol, further preferably from 0.005 to 0.5 mol, further preferably from 0.01 to 0.2 mol, further preferably from 0.02 to 0.1 mol; or such that the adhesive composition comprises the at least one metal in an oxidation state of II or higher relative to the weight, in kg, of the dry mass of the at least one compound that is capable of polymerizing and hydrogen bonding, in a concentration of from 0.002 to 20 mol, preferably from 0.05 to 5 mol, further preferably from 0.08 to 2 mol, further preferably from 0.1 to 1.5 mol.

That means that if anhydrous aluminum sulfate is used for preparing the adhesive composition, 1 kg of adhesive composition, including solvent, preferably comprises 0.0855 g to 855 g (0.0005 mol to 5 mol), further preferably 0.1711 g to 171.065 g (0.001 mol to 1 mol aluminum ions), more preferably 0.8553 g to 85.5325 g (0.005 to 0.5 mol aluminum ions), further preferably 1.711 g to 34.213 g (0.01 to 0.2 mol aluminum ions), further preferably 3.421 g to 17.1065 g (0.02 to 0.1 mol aluminum ions) aluminum sulfate.

Thus, in one embodiment, the present invention may be described as relating to an adhesive composition, comprising:
a) microfibrillated cellulose;
b) at least one metal in an oxidation state of II or higher that is derived from a metal ion source used for preparing the adhesive composition;
c) at least one compound that (a) is capable of polymerizing or has already partly or fully polymerized, and that (b) has at least two groups available for hydrogen bonding, preferably OH groups, that are capable of crosslinking with at least one functional group of the microfibrillated cellulose and/or the at least one metal in an oxidation state of II or higher;
d) at least one solvent,
wherein the adhesive composition comprises the metal ion source in an amount such that the relative amount, i.e. concentration, of the at least one a metal in an oxidation state of II or higher complies with at least one of the following:
(i) the amount of moles of the metal in an oxidation state of II or higher, relative to the weight, in kg, of the overall adhesive composition, including solvent, is from 0.005 to 5, preferably from 0.001 to 1, further preferably from 0.005 to 0.5, further preferably from 0.01 to 0.2, further preferably from 0.02 to 0.1;
(ii) the amount of moles of the metal in an oxidation state of II or higher, relative to the weight of the dry mass of the at least one compound that (a) is capable of polymerizing or has already partly or fully polymerized, and that (b) has at least two groups available for hydrogen bonding, preferably OH groups, that are capable of crosslinking with at least one functional group of the microfibrillated cellulose and/or the at least one metal in an oxidation state of II or higher, in kg, is from 0.002 to 20, preferably from 0.05 to 5, further preferably from 0.08 to 2, further preferably from 0.1 to 1.5, or
(iii) the metal in an oxidation state of II or higher is present as an oxide, hydroxide or oxyhydroxide, or any mixture thereof, and the weight percentage of said oxide, hydroxide or oxyhydroxide relative to the weight of the overall composition, including solvent, is from 0.001 to 3, preferably from 0.05 to 2, even more preferably from 0.06 to 1.5, even more preferably from 0.1 to 1, even more preferably from 0.1 to 0.4.

If, for example, the metal ion source is aluminum sulfate $(Al_2(SO_4)_3)$, the present invention preferably may be described as relating to an adhesive composition, comprising:
a) microfibrillated cellulose;
b) at least one aluminum in an oxidation state of II or higher that is derived from aluminum sulfate $(Al_2(SO_4)_3)$;
c) at least one compound that (a) is capable of polymerizing or has already partly or fully polymerized, and that (b) has at least two groups available for hydrogen bonding, preferably OH groups, that are capable of crosslinking with at least one functional group of the microfibrillated cellulose and/or the at least one metal in an oxidation state of or higher;
d) at least one solvent,
wherein the adhesive composition comprises said aluminum sulfate $(Al_2(SO_4)_3)$ in an amount of 0.0855 g to 855 g (0.0005 mol to 5 mol), preferably 0.1711 g to 171.065 g (0.001 mol to 1 mol aluminum ions), further preferably 0.8553 g to 85.5325 g (0.005 to 0.5 mol aluminum ions), further preferably 1.711 g to 34.213 g (0.01 to 0.2 mol aluminum ions), further preferably 3.421 g to 17.1065 g (0.02 to 0.1 mol aluminum ions) per kg of the total adhesive composition, including solvent.

The skilled person is able to calculate the amounts of other metal ion sources that result in an adhesive composition that comprises the at least one metal in an oxidation state of II or higher relative to the weight, in kg, of the overall adhesive composition, including solvent, in a concentration of from 0.0005 to 5 mol, preferably from 0.001 to 1 mol, further preferably from 0.005 to 0.5 mol, further preferably from 0.01 to 0.2 mol, further preferably from 0.02 to 0.1 mol.

For example, if sodium aluminate ($NaAlO_2$) provided as Gilunal A (from Kurita) with $Al_2O_3$ content of 54% is used as metal ion source, said sodium aluminate is preferably used in an amount of 0.047 g to 472 g, preferably 0.094 g to 94.4 g, more preferably 0.472 g to 47.2 g, more preferably 0.944 g to 18.9 g, more preferably 1.888 g to 9.441 g, per kg of the overall adhesive composition, including solvent.

Thus, if, for example, the metal ion source is sodium aluminate (solid powder with $Al_2O_3$ content of 54%) the present invention may be described as relating to an adhesive composition, comprising:
a) microfibrillated cellulose;
b) at least one aluminum in an oxidation state of or higher that is derived from sodium aluminate ($NaAlO_2$);
c) at least one compound that (a) is capable of polymerizing or has already partly or fully polymerized, and that (b) has at least two groups available for hydrogen bonding, preferably OH groups, that are capable of crosslinking with at least one functional group of the microfibrillated cellulose and/or the at least one metal in an oxidation state of II or higher;
d) at least one solvent,
wherein the adhesive composition comprises said sodium aluminate ($Al_2O_3/Na_2O$) in an amount of 0.047 g to 472 g, preferably 0.094 g to 94.4 g, more preferably 0.472 g to 47.2 g, more preferably 0.944 g to 18.9 g, more preferably 1.888 g to 9.441 g, per kg of the overall adhesive composition, including solvent.

Respective calculations can be performed by the skilled person for any metal ion source.

In the present invention it is generally preferred that if the metal in an oxidation state of II or higher is derived from sodium aluminate (for example in form of a solid powder with an $Al_2O_3$ content of around 54%), then said sodium aluminate is present in the adhesive composition in such an amount that 1 kg of overall adhesive composition comprise the metal in an oxidation state of II or higher (aluminum in this case) in an amount of from 0.02 to 0.1 mols. That means that if the metal in an oxidation state of II or higher is derived from sodium aluminate, then said sodium aluminate is present in the adhesive composition in an amount of 1.889 g to 9.441 g, per kg of the overall adhesive composition, including solvent.

In accordance with the present invention it is preferred that if the metal in an oxidation state of II or higher is zirconium (e.g. derived from ammonium zirconium (IV) carbonate solution with a zirconium content of around 15%), then said zirconium is present in the adhesive composition in such an amount that 1 kg of overall adhesive composition comprise the metal in an oxidation state of II or higher (zirconium in this case) in an amount of from 0.0005 to 0.1 mols, preferably from 0.001 to 0.05 mols. That means that if the metal in an oxidation state of II or higher is derived from an ammonium zirconium carbonate solution, then said ammonium zirconium carbonate is present in the adhesive composition in an amount of from 0.31 g to 62 g, preferably from 0.62 g to 31 g per kg of the overall adhesive composition, including solvent.

In accordance with the present invention it is preferred that if the metal in an oxidation state of II or higher is calcium (e.g. derived from calcium carbonate with 97% $CaCO_3$), then said calcium ion is present in the adhesive composition in such an amount that 1 kg of overall adhesive composition comprise the metal in an oxidation state of II or higher (calcium in this case) in an amount of from 0.05 to 5 mols, preferably from 0.1 to 3 mols. That means that if the metal in an oxidation state of II or higher is derived from calcium carbonate, then said calcium carbonate is present in the adhesive composition in an amount of from 5.2 g to 516 g, preferably from 10.3 g to 309 g per kg of the overall adhesive composition, including solvent.

Preferably, the solvent as used in the present compositions is a protic solvent. More preferably, the solvent comprises or consists of water.

Preferably, the MFC has at least one length scale, i.e. fibril diameter and/or fibril length, that is reduced vis-à-vis the fiber diameter and/or the fiber length of the non-fibrillated cellulose. Preferably, the diameter of the MFC fibrils making up the MFC of the present invention is in the nanometer range, i.e. from 1 nm to 1000 nm, preferably, and on average, from 10 nm to 500 nm. As described above, the fiber length and diameter can be determined by way of conventional optical microscopy, for example at a magnification of 40×, and/or by electron microscopy (SEM or TEM), depending on the dimension of the fibers.

Preferably, the amount of MFC in the adhesive composition is from 0.001 to 10 wt. %. More preferably, the amount of MFC in the adhesive composition is from 0.01 to 5 wt. %, even more preferably from 0.01 to 1 wt. %, even more preferably from 0.01 to 0.5 wt. %, even more preferably from 0.01 to 0.3 wt. %.

If the metal in an oxidation state of II or greater is derived from aluminum sulfate or if the adhesive composition comprises $Al^{3+}$ ions, the amount (weight) of MFC in the adhesive composition, relative to the weight of the overall adhesive composition, is preferably from 0.01 to 5 wt. %, more preferably from 0.01 to 1 wt. %, even more preferably from 0.01 to 0.5 wt. %, even more preferably from 0.01 to 0.3 wt. %.

Preferably, the amount of anhydrous aluminum sulfate in the overall adhesive composition is from 0.001 to 10 wt. % (w/w). More preferably, the amount of aluminum sulfate in the adhesive composition is from 0.01 to 5 wt. %, even more preferably from 0.015 to 2 wt. %, even more preferably from 0.03 to 0.5 wt. %. Alternatively, the amount of aluminum sulfate in the adhesive composition is from 0.01 to 0.25 wt. %, or from 0.1 to 1.3 wt %.

If the metal in an oxidation state of II or greater is derived from sodium aluminate or if the adhesive composition comprises $Al(OH)_4^-$ ions, the amount of MFC in the overall adhesive composition is preferably from 0.01 to 5 wt. %, more preferably from 0.01 to 1 wt. %, even more preferably from 0.01 to 0.5 wt. %, even more preferably from 0.01 to 0.3 wt. %.

Preferably, the equivalent amount of $Al_2O_3$ from sodium aluminate (or from aluminum sulfate or other aluminum compounds) in the overall adhesive composition is from 0.001 to 3% (w/w). More preferably, the amount of $Al_2O_3$ in the adhesive composition is from 0.05 to 2%, even more preferably from 0.06 to 1.5%, even more preferably from 0.1 to 1%, even more preferably from 0.1 to 0.4%.

Preferably, the at least one functional group of the MFC is selected from the groups of hydroxyl groups, carboxyl groups, ester groups, ether groups, aldehyde groups, preferably hydroxyl groups. These groups have been shown to lead to a particularly good crosslinking with the "at least one compound".

The solvent is preferably present in an amount of from 20 to 90 wt. % (w/w), preferably from 30 to 80 wt. %, more preferably from 40 to 80 wt. %, even more preferably from 50 to 80 wt. %. Even more preferably, the solvent is present in an amount of from 65 to 80 wt. %, preferably 69 to 79 wt. %, relative to the overall adhesive composition, respectively.

As stated above, the unique combination of MFC and a metal in an oxidation state of II or greater [such as $Al^{3+}$ or $Al(OH)_4^-$] allows for a complete omission of borax and/or boric acid without negatively affecting the overall properties of the adhesive composition.

Thus, according to a preferred embodiment, the adhesive composition comprises no or only trace amounts of boron-containing crosslinking agents.

Preferably, the adhesive composition comprises no or only trace amounts of borax and/or boric acid.

Even more preferably, the adhesive composition comprises no or only trace amounts of boron, irrespective of its origin and function. "Trace amounts" as used herein refer to amounts of less than 1000 ppm, preferably less than 500 ppm, further preferably less than 200 ppm, further preferably less than 100 ppm, further preferably less than 50 ppm.

Preferably, the weight ratio of MFC to the "at least one compound capable of polymerizing and hydrogen bonding" is from 0.0001 to 0.5, preferably from 0.0002 to 0.3, more preferably from 0.0004 to 0.2, even more preferably from 0.0005 to 0.1.

Preferably, the "at least one compound capable of polymerizing and hydrogen bonding" is selected from the following compounds:
- at least one starch or starch derivative, in particular dextrin,
- at least one polyvinyl alcohol,
- at least one polyvinyl acetate,
- at least one polyethylene glycol,
- at least one polypropylene glycol,
- at least one polysaccharide,
- at least one carbohydrate,
- at least one polypeptide,
- at least one acrylate,
- at least one acrylamide,
- at least one ethylene oxide,
- at least one propylene oxide,
- at least one glycol,
- at least one polyether,
- at least one polyester,
- at least one polyol,
- at least one epoxy resin,
- at least one polyurethane,
- at least one polyacrylate such as polymethylmethacrylate (PMMA),
- at least one polyurea and
- at least one carbamide.

Preferably, the "at least one compound capable of polymerizing and hydrogen bonding" is at least one starch or starch derivative, or at least one polyvinyl alcohol.

Preferably, if the "at least one compound capable of polymerizing and hydrogen bonding" is at least one polyvinyl alcohol, the pH of the adhesive composition is below 7, preferably from 2.0 to 6, more preferably from 2.5 to 5.0.

Preferably, if the "at least one compound capable of polymerizing and hydrogen bonding" is at least one starch or starch derivative, the pH of the adhesive composition is above 7, preferably from 10 to 13, further preferably from 10.5 to 12.5 or from 11 to 12.

According to a preferred embodiment, the aluminum ion is $Al(OH)_4^-$ and/or is derived from sodium aluminate and the "at least one compound capable of polymerizing and hydrogen bonding" is at least one starch or starch derivative.

In embodiments, the amount of microfibrillated cellulose in said (starch-based) adhesive composition is from 0.001 to 10 wt %, preferably 0.01 to 5 wt. %, more preferably from 0.01 to 1 wt. %, even more preferably from 0.01 to 0.5 wt. %, even more preferably from 0.01 to 0.3 wt. %, based on the total weight of the adhesive composition.

In preferred embodiments, the amount of microfibrillated cellulose in said (starch-based) adhesive composition is from 0.01 to 0.25% wt %.

Also in this embodiment, the solvent is preferably present in an amount of from 20 to 90 wt. % (w/w), preferably from 30 to 80 wt. %, more preferably from 40 to 80 wt. %, even more preferably from 50 to 80 wt. %. Even more preferably, the solvent is present in an amount of from 65 to 80 wt. %, preferably 66 to 79 wt. %, based on the total weight of the adhesive composition.

Also in this embodiment, the weight ratio of MFC to the "at least one compound" preferably is from 0.0001 to 0.5, preferably from 0.0002 to 0.3, more preferably from 0.0004 to 0.2, even more preferably from 0.0005 to 0.1, even more preferably from 0.0005 to 0.03, even more preferably from 0.001 to 0.01 (MFC to starch).

Preferably, the amount of starch in the adhesive composition is from 10 to 60 wt. %, more preferably from 15 to 45 wt. %, even more preferably from 20 to 40 wt. %.

According to another preferred embodiment, the aluminum ion is derived from aluminum sulfate and the "at least one compound" is at least one polyvinyl alcohol.

In embodiments, the amount of microfibrillated cellulose in said (PVA-based) adhesive composition is from 0.001 to 10 wt %, preferably from 0.01 to 5 wt. %, more preferably from 0.015 to 1 wt. %, even more preferably from 0.02 to 0.5 wt. %, even more preferably from 0.05 to 0.3 wt. %, based on the total weight of the adhesive composition.

In preferred embodiments, the amount of microfibrillated cellulose in said (PVA-based) adhesive composition is from 0.05 to 0.25% wt %.

Also in embodiments, the solvent is preferably present in an amount of from 20 to 90 wt. % (w/w), preferably from 30 to 80 wt. %, more preferably from 40 to 80 wt. %, even more preferably from 50 to 80 wt. %. Even more preferably, the solvent is present in an amount of from 65 to 80 wt. %, preferably 69 to 79 wt. %, based on the total weight of the adhesive composition.

Also in embodiments, the weight ratio of MFC to the "at least one compound" preferably is from 0.0001 to 0.5, preferably from 0.0002 to 0.3, more preferably from 0.0004 to 0.2, even more preferably from 0.0005 to 0.1, even more preferably from 0.005 to 0.1, even more preferably from 0.008 to 0.08 (MFC to polyvinyl alcohol).

Preferably, the amount of PVA in the adhesive composition is from 1 to 30 wt. %, more preferably from 2 to 28 wt. %, even more preferably from 3 to 25 wt. %, even more preferably from 3 to 10 wt. %.

In embodiments of the present invention, further additives may be used in the adhesive compositions according to the present invention, such as calcium chloride, sodium hydroxide, urea, sodium nitrate, thiourea and guanidine salts, some or all of which may be used as liquefiers to (further) control viscosity.

Other embodiments that may be used in the adhesive compositions according to the present invention are, e.g., preservatives, bleaches, and defoamers.

According to a second embodiment, the present invention relates to the use of an adhesive composition according to the present invention for the preparation of corrugated boards or solid boards, in particular cardboards or paperboards.

As noted above and as it is evident from the examples, the adhesive composition according to the present invention is particularly suitable for manufacturing corrugated boards or solid boards.

In particular, it has surprisingly been found that the unique combination of MFC and an aluminum ion or polyatomic aluminum-containing ion leads to synergistic effects resulting in surprisingly good overall adhesive properties even in the complete absence of borax. Such properties have not been observed before for a borax-free adhesive composition.

Specifically, it has been shown that the inventive adhesive composition allows for using high corrugator running speeds for all, including the most difficult to achieve qualities of boards. In fact, it has been shown that the inventive adhesive compositions perform better than adhesive composition on borax basis and also better than adhesive glues on MFC (only) basis or on borax/MFC basis.

Also, it has been shown that the inventive adhesive composition shows a similar initial tackiness as a boric acid-containing PVA (polyvinyl alcohol)-adhesive composition, but, at the same time, shows significantly decreased water uptake, which is particularly beneficial for preparing solid boards, which are frequently used in moist environments like agriculture or for packaging seafood. These and other surprising effects render the adhesive compositions particularly suitable for preparing corrugated or solid boards (cardboards or paperboards).

In one embodiment, the adhesive composition according to the present invention is used for preparing corrugated boards. In this embodiment, the metal in an oxidation state of II or greater is preferably $Al(OH)_4^-$ and/or derived from sodium aluminate and the "at least one compound capable of polymerizing and hydrogen bonding" is preferably at least one starch or starch derivative.

In another embodiment, the adhesive composition according to the present invention is used for preparing solid boards. In this embodiment, the metal in an oxidation state of II or greater is preferably $Al^{3+}$ and/or is derived from aluminum sulfate, and the "at least one compound capable of polymerizing and hydrogen bonding" is at least one polyvinyl alcohol.

According to a third embodiment, the present invention relates to the use of a combination of MFC and a metal in an oxidation state of II higher, preferably a monoatomic aluminum ion or a polyatomic aluminum-containing ion, preferably $Al^{3+}$ or $Al(OH)_4^-$, wherein said $Al^{3+}$ is preferably derived from aluminum sulfate and said $Al(OH)_4^-$ is preferably derived from sodium aluminate, for preparing an adhesive composition as defined herein.

According to a fourth embodiment, the present invention relates to a corrugated board and a solid board comprising the inventive adhesive composition.

Preferably, a corrugated board comprises the inventive adhesive composition, wherein the aluminum ion or polyatomic aluminum-containing ion is $Al(OH)_4^-$ and/or derived from sodium aluminate, and the "at least one compound" is at least one starch or starch derivative.

Preferably, a solid board comprises the inventive adhesive composition, wherein the aluminum ion or polyatomic aluminum-containing ion is $Al^{3+}$ and/or derived from aluminum sulfate, and the "at least one compound" is at least one polyvinyl alcohol.

According to a fifth embodiment, the present invention relates to a process for making corrugated boards. This process at least comprises the following steps:
a) providing an adhesive composition according to the present invention;
b) providing fluting paper and liner paper for corrugated boards; optionally wherein said paper for the flutes or for the liners, or both, is or has/have been at least partly chemically treated;
c) applying said adhesive composition to at least a part of the tips of the flutes of a corrugated piece of paper, on at least one side, preferably on both sides; and:
d) in a corrugator, applying at least one liner onto said corrugated piece of paper, preferably applying a further liner on the other side of the corrugated piece of paper, and
e) preparing a single, double, triple or further multiple wall board, preferably in a continuous process.

The present invention may also be described in terms of the following items, which may be combined with each and all of the embodiments described above:

Item 1. Adhesive composition, comprising:
a) microfibrillated cellulose;
b) at least one metal in an oxidation state of II or higher;
c) at least one compound that (a) is capable of polymerizing or has already partly or fully polymerized, and that (b) has at least two groups available for hydrogen bonding, preferably OH groups, that are capable of crosslinking with at least one functional group of the microfibrillated cellulose and/or the at least one metal in an oxidation state of II or higher;
d) at least one solvent,
wherein the relative amount of the at least one metal in an oxidation state of II or higher complies with at least one of the following:
(i) the amount of moles of the metal in an oxidation state of II or higher, relative to the weight, in kg, of the overall adhesive composition, including solvent, is from 0.0005 to 5, preferably from 0.001 to 1, further preferably from 0.005 to 0.5, further preferably from 0.01 to 0.2, further preferably from 0.02 to 0.1,
(ii) the amount of moles of the metal in an oxidation state of II or higher, relative to the weight of the dry mass of the at least one compound that (a) is capable of polymerizing or has already partly or fully polymerized, and that (b) has at least two groups available for hydrogen bonding, preferably OH groups, that are capable of crosslinking with at least one functional group of the microfibrillated cellulose and/or the at least one metal in an oxidation state of II or higher, in kg, is from 0.002 to 20, preferably from 0.05 to 5, further preferably from 0.08 to 2, further preferably from 0.1 to 1.5; or
(iii) the metal in an oxidation state of II or higher is present as an oxide, hydroxide or oxyhydroxide, or any mixture thereof, and the weight percentage of said oxide, hydroxide or oxyhydroxide relative to the weight of the overall composition, including solvent, is from 0.001 to 3, preferably from 0.05 to 2, even more preferably from 0.06 to 1.5, even more preferably from 0.1 to 1, even more preferably from 0.1 to 0.4.

Item 2. The adhesive composition according to item 1, wherein the metal in an oxidation state of II or higher comprises Aluminum in an oxidation state of II or higher, Calcium in an oxidation state of II or higher, Zirconium in an oxidation state of II or higher, Magnesium in an oxidation state of II or higher, Zink in an oxidation state of II or higher, Hafnium in an oxidation state of II or higher or Titanium in an oxidation state of II or higher, or any combination thereof, preferably comprises Aluminum in an oxidation state of II or higher.

Item 3. The adhesive composition according to item 1 or 2, wherein said metal in an oxidation state of II or higher comprises an aluminum ion, and is preferably derived from aluminum sulfate, sodium aluminate or aluminum hydroxide.

Item 4. The adhesive composition according to any one of the preceding items, wherein the solvent is a protic solvent.

Item 5. The adhesive composition according to item 4, wherein the solvent comprises or consists of water.

Item 6. The adhesive composition according to any one of the preceding items, wherein the microfibrillated cellulose has at least one length scale, i.e. fibril diameter and/or fibril length, that is reduced vis-à-vis the fiber diameter and/or the fiber length of the non-fibrillated cellulose; preferably wherein the diameter of the microfibrillated cellulose fibrils making up the microfibrillated cellulose of the present invention is in the nanometer range, i.e. from 1 nm to 1000 nm, preferably, and on average, from 10 nm to 500 nm.

Item 7. The adhesive composition according to any one of the preceding items, wherein the amount of microfibrillated cellulose in said adhesive composition is from 0.001 to 10 wt. %. (w/w), preferably from 0.01 to 5 wt. %, even more preferably from 0.01 to 1 wt. %, even more preferably from 0.01 to 0.5 wt. %, even more preferably from 0.01 to 0.3 wt. %, based on the total weight of the adhesive composition.

Item 8. The adhesive composition according to any one of the preceding items, wherein the at least one functional group of the microfibrillated cellulose is selected from hydroxyl groups, carboxyl groups, ester groups, ether groups, and aldehyde groups.

Item 9. The adhesive composition according to any one of the preceding items, wherein the solvent is present in an amount of from 20 to 90 wt. %, preferably from 30 to 80 wt. %, more preferably from 40 to 80 wt. %, even more preferably from 50 to 80 wt. %, such as from 65 to 80 wt. %, preferably 66 to 79 wt. %, based on the total weight of the adhesive composition.

Item 10. The adhesive composition according to any one of the preceding items, wherein the composition comprises no or only trace amounts of boron-containing crosslinking agents, preferably wherein the adhesive composition comprises no or only trace amounts of borax and boric acid, further preferably wherein the adhesive composition preferably comprises no or only trace amounts of boron.

Item 11. The adhesive composition according to any one of the preceding items, wherein the weight ratio of microfibrillated cellulose to the at least one compound that (a) is capable of polymerizing or has already partly or fully polymerized, and that (b) has at least two groups available for hydrogen bonding, preferably OH groups, that are capable of crosslinking with at least one functional group of the microfibrillated cellulose and/or the at least one metal in an oxidation state of II or higher, is from 0.0001 to 0.5, preferably from 0.0002 to 0.3, more preferably from 0.0004 to 0.2, even more preferably from 0.0005 to 0.1 or 0.0005 to 0.03 or 0.001 to 0.01.

Item 12. The adhesive composition according to any one of the preceding items, wherein the compound that (a) is capable of polymerizing, or has already partly or fully polymerized, and that (b) has at least two groups available for hydrogen bonding, preferably OH groups, that are capable of crosslinking with at least one functional group of the microfibrillated cellulose and/or the at least one metal in an oxidation state of II or higher is selected from the following compounds:

at least one starch or starch derivative, at least one polyvinyl alcohol, at least one polyvinyl acetate, at least one polyethylene glycol, at least one polypropylene glycol, at least one polysaccharide, at least one carbohydrate, at least one polypeptide, at least one acrylate, at least one acrylamide, at least one ethylene oxide, at least one propylene oxide, at least one glycol, at least one polyether, at least one polyester, at least one polyol, at least one epoxy resin, at least one polyurethane, at least one polyacrylate such as polymethylmethacrylate (PMMA), at least one polyurea and at least one carbamide, or any combination thereof;

preferably from at least one starch or starch derivative, and at least one polyvinyl alcohol.

Item 13. The adhesive composition according to any one of the preceding items, wherein the metal in an oxidation state of II or higher is present as $Al(OH)_4^-$ and/or is derived from sodium aluminate and wherein the compound that is (a) capable of polymerizing, or has already partly or fully polymerized, and that (b) has at least two groups available for hydrogen bonding, preferably OH groups, that are capable of crosslinking with at least one functional group of the microfibrillated cellulose and/or the at least one metal in an oxidation state of II or higher, is at least one starch or starch derivative.

Item 14. The adhesive composition according to item 13, wherein the amount of microfibrillated cellulose in said starch-based adhesive composition is from 0.001 to 10 wt %, preferably from 0.01 to 5 wt. %, even more preferably from 0.01 to 1 wt. %, even more preferably from 0.01 to 0.5 wt. %, even more preferably from 0.01 to 0.3 wt. %, based on the total weight of the adhesive composition.

Item 15. The adhesive composition according to item 13 or 14, wherein the weight ratio of microfibrillated cellulose to the at least one compound that is (a) capable of polymerizing or has already partly or fully polymerized, and that (b) has at least two groups available for hydrogen bonding, preferably OH groups, that are capable of crosslinking with at least one functional group of the microfibrillated cellulose and/or the at least one metal in an oxidation state of II or higher, is from 0.0001 to 0.5, preferably from 0.0002 to 0.3, more preferably from 0.0004 to 0.2, even more preferably from 0.0005 to 0.1, even more preferably from 0.0005 to 0.03, even more preferably from 0.001 to 0.01.

Item 16. The adhesive composition according to any one of items 1 to 12, wherein the metal in an oxidation state of II or higher is present as $Al^{3+}$ and/or is derived from aluminum sulfate and wherein the compound that is (a) capable of polymerizing, or has already partly or fully polymerized, and that (b) has at least two groups available for hydrogen bonding, preferably OH groups, that are capable of crosslinking with at least one functional group of the microfibrillated cellulose and/or the at least one metal in an oxidation state of II or higher, is at least one polyvinyl alcohol (PVA).

Item 17. The adhesive composition according to item 16, wherein the amount of microfibrillated cellulose in said PVA-based adhesive composition is from 0.001 to 10 wt %, preferably from 0.01 to 5 wt. %, even more preferably from 0.015 to 1 wt. %, even more preferably from 0.02 to 0.5 wt. %, even more preferably from 0.05 to 0.3 wt, based on the total weight of the adhesive composition.

Item 18. The adhesive composition according to any one of items 16 or 17, wherein the weight ratio of microfibrillated cellulose to the at least one compound that is (a) capable of polymerizing or has already partly or fully polymerized, and that (b) has at least two groups available for hydrogen bonding, preferably OH groups, that are capable of crosslinking with at least one functional group of the microfibrillated cellulose and/or the at least one metal in an oxidation state of II or higher, is from 0.0001 to 0.5, preferably from 0.0002 to 0.3, more preferably from 0.0004 to 0.2, even more preferably from 0.0005 to 0.1, even more preferably from 0.005 to 0.1, even more preferably from 0.008 to 0.08.

Item 19. Use of an adhesive composition according to any one of items 1 to 18 for the preparation of corrugated boards or solid boards.

Item 20. The use according to item 19 for the preparation of corrugated boards, wherein the metal in an oxidation state of II or higher is present as $Al(OH)_4^-$ and/or derived from sodium aluminate, and
the compound that is (a) capable of polymerizing, or has already partly or fully polymerized, and that (b) has at least two groups available for hydrogen bonding, preferably OH groups, that are capable of crosslinking with at least one functional group of the microfibrillated cellulose and/or the at least one metal in an oxidation state of II or higher. is at least one starch or starch derivative.

Item 21. The use according to item 19 for the preparation of solid boards, wherein the metal in an oxidation state of II or higher is present as $Al^{3+}$ and/or derived from aluminum sulfate, and
the compound that is (a) capable of polymerizing, or has already partly or fully polymerized, and that (b) has at least two groups available for hydrogen bonding, preferably OH groups, that are capable of crosslinking with at least one functional group of the microfibrillated cellulose and/or the at least one metal in an oxidation state of II or higher, is at least one polyvinyl alcohol.

Item 22. Use of an adhesive composition according to any one of items 1 to 18 as an adhesive, in a paint composition, as a coating, as a (surface) size composition, as or in a composite, as a resin, as a paste, as a food thickener or additive, in a gel, in a hydrogel or as an absorbent or in adhesive coatings, protective coatings, primer coatings, surface sizing coatings.

Item 23. A corrugated or solid board comprising an adhesive composition as defined in any one of items 1 to 18.

Item 24. A corrugated board comprising an adhesive composition as defined in any one of items 13 to 15.

Item 25. A solid board comprising an adhesive composition as defined in any one of items 16 to 18.

Item 26. Process for making corrugated boards, said process comprising at least the following steps:
a) providing an adhesive composition as defined in any one of items 1 to 18;
b) providing fluting paper and liner paper for corrugated boards; optionally wherein said paper for the flutes or for the liners, or both, is or has/have been at least partly chemically treated;
c) applying said adhesive composition to at least a part of the tips of the flutes of a corrugated piece of paper, on at least one side, preferably on both sides; and:
d) in a corrugator, applying at least one liner onto said corrugated piece of paper, preferably applying a further liner on the other side of the corrugated piece of paper, and
e) preparing a single, double, triple or further multiple wall board, preferably in a continuous process.

Item 27. Corrugated board obtained by or obtainable by a process according to item 26.

EXAMPLES

Example 1

Preparation of Microfibrillated Cellulose (MFC)

MFC as used to prepare the compositions in accordance with the present invention is commercially available and commercialized, for example, by Borregaard as "Exilva Microfibrillated cellulose FBX 01-V", or "Exilva Microfibrillated cellulose P01-L", based on cellulose pulp from Norwegian spruce (softwood).

The MFC used in the examples relating to starch as the compound capable of polymerizing and hydrogen bonding was present as a paste, having a solids content of 10%, i.e. the dry matter content of microfibrillated fibers in the MFC paste was 10%, while the remaining 90% were water, which was the sole solvent in this case.

The MFC used in the examples relating to polyvinyl alcohol (PVA) as the compound capable of polymerizing and hydrogen bonding was present as a dispersion, having a solids content of 2%, i.e. the dry matter content of microfibrillated fibers in the MFC paste was 2%, while the remaining 98% were water, which was the sole solvent in this case.

Example 2

Improving the Properties of a Starch-Containing Adhesive Composition; Effect on Corrugator Speed and Adhesiveness [MFC and Sodium Aluminate (Solid)]

The compositions shown in Table 1 were prepared according to the following protocol: The adhesives were prepared according to the Stein-Hall process. The primary starch portion was added to the primary water portion, at a temperature of 39° C., and stirred for 30 seconds before the addition of caustic soda. Then the primary starch was stirred for 500 seconds, before the addition of MFC. The primary starch and MFC was then stirred for another 600 seconds, followed by the addition of the secondary water portion and disinfectant. The temperature of the composition was 31° C. after the addition of the secondary water portion. The secondary starch portion was then added; the composition was stirred for 30 seconds and then the sodium aluminate was added. Then the composition was stirred for 200 seconds, before the final stirring time of 200+/−700 seconds until a viscosity set point of 35 Lory seconds was achieved. For compositions comprising borax, ⅓ of the borax was added before the addition of secondary starch, and ⅔ of the borax was added after the addition and 30 seconds mixing time of the secondary non-swollen starch.

Lory viscosity was measured with a Lory viscosity cup (Elcometer 2215/1), which is commonly used in the adhesive, paint and coatings industry and which essentially consists of a conventional cylindrical cup with a needle fixed to the bottom. The cup is first dipped into the adhesive, which then empties through an escape hole. The flow time was measured as soon as the point of the needle was visible.

The Lory viscosity of the comparative starch-based adhesive comprising only borax (Composition no. 2) did decrease readily with mixing time at high shear, whereas the viscosity of the adhesives comprising MFC (Compositions 1, 3 and 4) were considerably more viscosity stable towards the high shear mixing. Moreover, the compositions comprising MFC were far more viscosity stable over time, compared to the borax reference adhesive.

TABLE 1

|  | Composition No. 1 (inventive) | | Composition No. 2 (comparative, borax only reference) | | Composition No. 3 (comparative; MFC only, but no metal ion) | | Composition No. 4 (comparative, MFC and borax, no metal ion; results shown in Table 4) | |
| --- | --- | --- | --- | --- | --- | --- | --- | --- |
| Component | amount (kg) | % | amount (kg) | % | amount (kg) | % | amount (kg) | % |
| Primary water | 400 | 25.0 | 450 | 34.4 | 400 | 25.0 | 450 | 32.9 |
| Primary starch | 48 | 3.0 | 42 | 3.2 | 42 | 2.6 | 41 | 3.0 |
| Water | 70 | 4.4 | 70 | 5.3 | 70 | 4.4 | 70 | 5.1 |
| Caustic soda (31%) | 12 | 0.7 | 13 | 1.0 | 12 | 0.8 | 12 | 0.9 |
| Exilva Fbx 01-V | 13 | 0.8 | 0 | 0.0 | 25 | 1.6 | 10 | 0.7 |
| Secondary water | 540 | 33.7 | 410 | 31.3 | 540 | 33.8 | 410 | 30.0 |
| Disinfectant | 1 | 0.1 | 1 | 0.1 | 1 | 0.1 | 1 | 0.1 |
| Secondary starch | 510 | 31.8 | 320 | 24.4 | 510 | 31.9 | 370 | 27.1 |
| Borax (Fullbor W6364) | 0 | 0.0 | 3 | 0.2 | 0 | 0.0 | 3 | 0.2 |
| Sodium aluminate (Gilunal A) | 8 | 0.5 | 0 | 0.0 | 0 | 0.0 | 0 | 0 |
| Total glue | 1602.0 | 100.0 | 1309.0 | 100.0 | 1600.0 | 100.0 | 1367.0 | 100.0 |
| DS % (commercial, only starch calc.) | 34.8 | | 27.7 | | 34.5 | | 30.1 | |
| DS % absolute (dry solids content, "dry matter") | 31.4 | | 24.8 | | 30.7 | | 26.9 | |

The starch was native wheat starch, supplied by Amilina/Roquette. The borax was Fullbor W6364, commercially available from HB Fuller, and the sodium aluminate was Gilunal A ($Al_2O_3$ content: 53-55%), commercially available from Kurita. The dry solids content (DS) was calculated both commercial (starch amount on total glue) and absolute (all components and adjusted for dry solids in each component) for all compositions. The pH of the glues was between 11.5-11.7.

Figure 6:
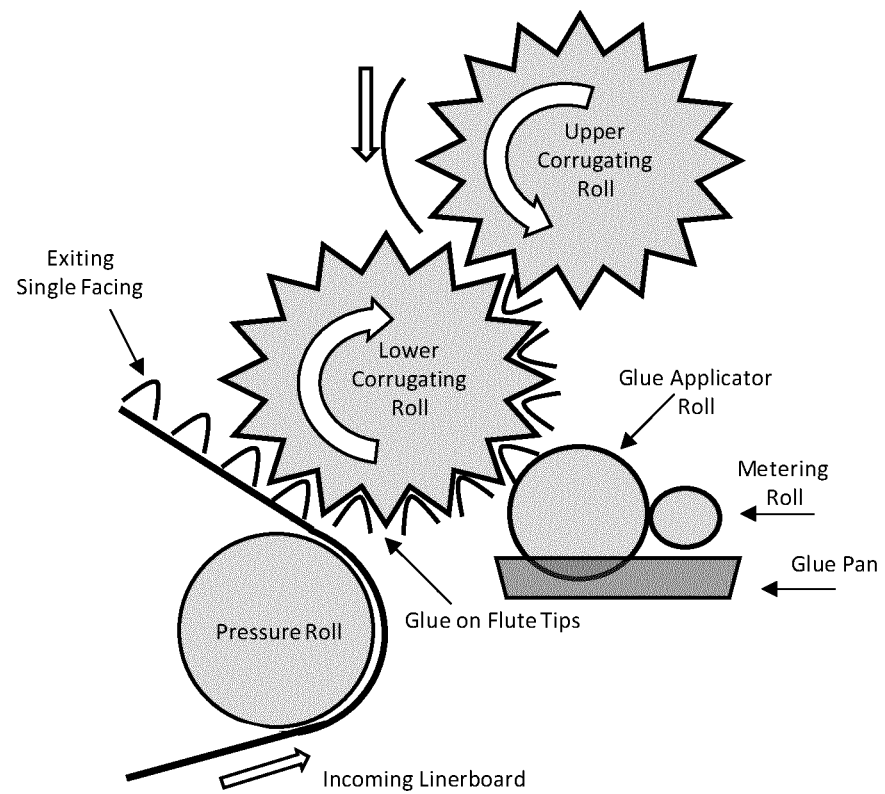
FIG. 6 schematically depicts a continuous production line for making corrugated cardboard (single facer).
Figure 7:
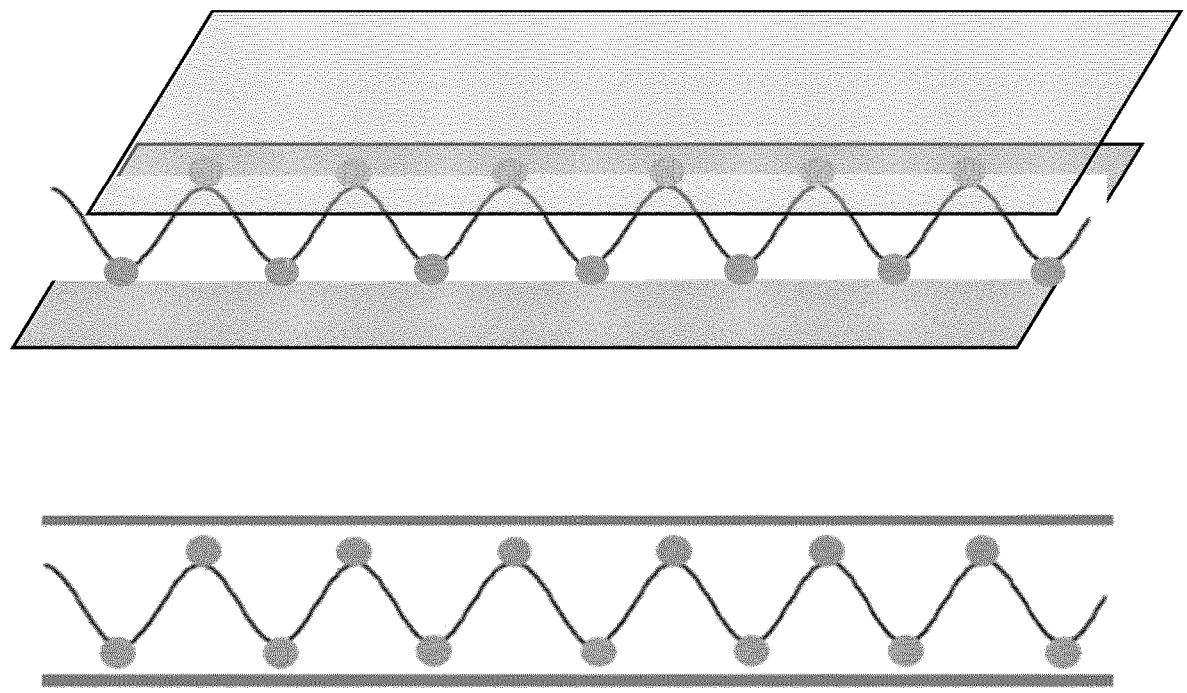
FIG. 7 schematically depicts a layer of cardboard comprising one layer of corrugated paper having the flutes tips coated with adhesive as well as an upper and a lower liner. A schematic illustration of "fluted" ("corrugated") piece of paper, i.e. a piece of paper that has been brought into contact with heat or steam, or both, on corrugating rolls, in order to have a corrugated ("fluted") shape is illustrated, which also shows how to exemplary apply glue to the tips of the flutes. The figure also illustrates an upper and a lower liner as applied onto the upper and lower tips of the fluted paper, called single facer and double backer side of the board, resulting in a single walled cardboard.

The compositions shown in Table 1 were then used for preparing corrugated boards according to the following protocol:

The starch adhesives, compositions 1-4, were tested in the production of corrugated boards, by a corrugator from BHS (wet end) and Fosber (dry end). A corrugator is a set of machines designed to bring together several sheets of papers to form single, double or triple wall corrugated boards in a continuous process. The process starts with a paper sheet conditioned with heat and steam on corrugating rolls, in order to be given its fluted shape in the single facer. The starch adhesive is then applied to the tips of the flutes on one side, and the inner liner is glued to the fluting (see FIGS. 6 and 7). The corrugated fluting medium with one liner attached to it (single facer) is then brought to the double backer where the outer liner is glued to the single facer.

The corrugator production speed achieved for a single wall B-flute quality, and double wall EB- and BC-flutes qualities for the different adhesive compositions 1, 2 and 3 is given in Table 2.

As it is evident from Table 2, the inventive adhesive composition allows for a significantly increased production speed on all qualities of corrugated boards and paper combinations tested, compared to a borax only reference composition. Further, the inventive adhesive composition allows for significantly increased production speeds as compared to an "MFC only" reference composition. On the heaviest and most challenging BC combination comprising semi-chemical fluting paper, the glue ability with the inventive adhesive composition was surprisingly significantly better, improving both the run ability and the production speed compared to the borax only and the MFC only reference compositions.

The initial bond strength of the semi-cured corrugated boards was measured during and after the production by hand tearing by a person skilled in the art; and the results are graded according to a scale where 1 is the lowest and 4 is the highest (initial bond strength). The final adhesion strength in Newton (N)/m was measured by the Pin Adhesion Test (PAT), according to the Fefco no. 11 standard, after curing and conditioning under controlled temperature and humidity. The standard test methods are outlined in Table 3.

TABLE 3

| Standard tests | | |
| --- | --- | --- |
| Conditions | Grammage | Adhesion strength |
| 23° C. - 50RH % ISO 187 | $g/m^2$ ISO 536 | N/m Fefco no. 11 |

TABLE 2

| | | Corrugator speed (m/min) | | |
| --- | --- | --- | --- | --- |
| Quality corrugated boards | Paper combinations | Composition No. 1 (in accordance with invention) | Composition No. 2 (comparative) | Composition No. 3 (comparative) |
| Quality B | 115TL/110SC/135WL | 350 | 300 | 250 |
| Quality EB | 135WL/100WF/100WF/100WF/135EK | 300 | 200 | 212 |
| Quality BC | 135EK/110SC/100WF/100WF/135EK | 250 | 160 | 200 |
| Quality BC Heavy with semi-chemical fluting | 250KL/110SC/180EK/110SC/250KL | 125 | 100 | 80/frequent delamination |

In Table 4, the bond strengths of the corrugated boards measured by hand tearing and by the Pin Adhesion Test on the Single Facer (SF) and the Double Backer (DB) sides of a B-flute quality 115EK/100WF/115EK produced with the adhesive compositions 1, 2, 3 and 4 are shown. The adhesive compositions comprising microfibrillated cellulose show an increase in the PAT-DB values measured in N/m of the corrugated boards, compared to the "borax only" composition. The inventive adhesive composition results by far in the highest adhesive strength measured in the PAT. The MFC and sodium aluminate composition increases the PAT value for the Single Facer by +57%, compared to the MFC and borax composition. The inventive adhesive composition also results in the highest initial or semi-cured bond strength, evaluated by hand tearing of the boards, and compared to the borax or MFC only, or to the MFC and borax composition.

TABLE 4

| Composition | Gap - SF (mm) | PAT - SF (N/m) | Gap - DB (mm) | PAT - DB (N/m) | Bond strength by hand tearing (1-4) |
|---|---|---|---|---|---|
| Composition No. 2 | n.d | n.d | 0.09 | 229 | 1-2 |
| Composition No. 3 | n.d | n.d | 0.09 | 370 | 1-2 |
| Composition No. 4 | 0.13 | 656 | 0.12 | 674 | 3-4 |
| Composition No. 1 | 0.11 | 1027 | n.d. | n.d. | 4 |

*n.d. = not determined

Without wishing to be bound by theory, it is believed that these surprising results can be explained by the improved wettability, penetration and elasticity (high storage modulus) of the adhesive, provided by the addition of microfibrillated cellulose, combined by the increased hydrogen-bonding cross-linking capability of the adhesive upon heat, provided by the presence of MFC having available OH groups and the presence of dissolved sodium aluminate, which are believed to act synergistically, i.e. the combined contribution to stability, elasticity and adhesiveness is greater than when adding the contribution from each component individually. One other explanation for the significantly improved strength of the semi-cured and final cured glue bonds, may be that a larger part of the raw starch is gelatinized, whereas the MFC is entrapping the starch granules and retaining the moisture around the granules, the aluminum ions may provide a more uniform and higher heat transfer rate, enhancing the adhesiveness. Another explanation is believed to be that the dissolved sodium aluminate may directly, or by bridging, improve the interaction with the fibres of the paper surfaces. It is generally known that sodium aluminate is used in the paper industry for increasing the paper strength. At pH ca. 11.5 (such as for the starch adhesives), molecular dynamics simulations have shown that aluminate ions interact strongly to the bonding of polyvalent positive ions on surfaces, as well as interfacial hydrogen bonds.

Without being bound by theory, it is believed that the nature of alkaline (high pH) aluminate solutions of sodium aluminate; having tetrahedral $Al(OH)_4^-$ as the predominant aluminum bearing compound at low concentration, leads to condensation to form $Al_2O(OH)_5^{2-}$ at higher concentrations.

Overall, all boards comprising MFC in the adhesive composition were flatter than the boards without MFC.

Overall, when using the combination of MFC and sodium aluminate in accordance with the present invention, a significant improvement of the glue-ability is achieved, expressed by the high increase in production speed and bond strength of the corrugated boards compared to the reference borax only glue. Even an increase of up to 56% in production speed could be achieved for the combination of MFC and sodium aluminate adhesive, compared to the borax only reference adhesive. On corrugated board qualities of "medium" complexity, boron free adhesives with MFC only have good performance. However, the current results clearly show that the running speed and board quality is further improved when using the inventive adhesive composition. Thus, the inventive adhesive enables the use of the same (boron-free) adhesive for all corrugated board qualities, which is a big advantage for the industry.

In summary, it has been found that the inventive adhesive composition shows high stability in process and during storage, gives very good gluing performances, results in flat boards and allows for high production speeds on all board qualities.

The results are further supported by laboratory experiments showing the superior effect of the combination of MFC and aluminate on the adhesive properties.

The Brookfield viscosity, storage modulus (elasticity) and water retention for starch only, MFC only, sodium aluminate only and the inventive MFC and sodium aluminate adhesives are shown in FIG. 5. The lab recipes and preparation procedure of the respective adhesives are given in Table 5.

As it can be seen from FIG. 5, upper three panels, sodium aluminate alone does not noticeably contribute to the Brookfield viscosity. MFC, however, significantly increases the viscosity of the glue.

The combination of MFC and sodium aluminate leads to as high a viscosity, while significantly improving water retention vis-à-vis the otherwise same adhesive, however, without the metal ion (here: aluminate).

As opposed to conventional adhesives without MFC, the two adhesives with a storage modulus of 31 Pa as shown in FIG. 5 (both comprising MFC) exhibit a predominantly elastic behavior in the linear viscoelastic range and the plateau value is determined.

The data of FIG. 5 overall show that the combination of MFC and sodium aluminate leads to a gel-like material and therefore indicates a better ability to stabilize both gelatinized and raw starch.

Sodium aluminate contributes relatively little to the water retention of the adhesive since the water retention value of adhesive comprising sodium aluminate is similar to the water retention value of the adhesive containing no additive.

The water retention value of the combination of MFC and sodium aluminate is higher than that of the equivalent single additive adhesive.

From FIG. 5, lower panel, it is clearly discernible that the presence of MFC leads to a higher viscosity at low shear rate while maintaining pronounced shear thinning behavior. A high viscosity at low shear enables the adhesive to keep the gelatinized and raw starch in suspension. This indicates that the presence of MFC, even in combination with sodium aluminate, gives the opportunity to formulate more stable adhesives while maintaining easy processability.

Overall, sodium aluminate alone, does not contribute significantly to the viscosity, storage modulus or water retention of the adhesive, whereas combinations of aluminate and MFC clearly improves the rheological properties and water retention. Gelatinization tests further show that a combination of aluminate and MFC results in a gelatinization profile comparable to a borax reference glue. The results illustrate the superior adhesive of the invention, having a unique combination of rheological properties, water retention values and gelatinization profile beneficial for the manufacturing of corrugated boards. Similar results have been obtained also with corn starch.

Table 5 Recipes and procedures for Laboratory experiments (FIG. 5)

| Component | Composition No. 5 (inventive: starch based adhesive with MFC and metal ion) amount (g) | % | Composition No. 6 (comparative: starch only) amount (g) | % | Composition No. 7 (comparative: starch/ MFC) amount (g) | % | Composition No. 8 (comparative: starch/ aluminate) amount (g) | % |
|---|---|---|---|---|---|---|---|---|
| Primary water | 142.55 | 28.9 | 146.24 | 29.9 | 142.55 | 29.1 | 146.24 | 29.7 |
| Primary starch (native wheat) | 13.07 | 2.7 | 13.07 | 2.7 | 13.07 | 2.7 | 13.07 | 2.7 |
| Temp. 42° C. | | | | | | | | |
| Stirring 15 sec at 2000 rpm | | | | | | | | |
| Temp. 41° C. | | | | | | | | |
| Caustic soda (31%) | 3.73 | 0.8 | 3.73 | 0.8 | 3.73 | 0.8 | 3.73 | 0.8 |
| Stirring 500 sec at 2000 rpm | | | | | | | | |
| Exilva Fbx 01-V | 4.10 | 0.8 | | | 4.10 | 0.8 | | |
| Stirring 500 sec at 2000 rpm | | | | | | | | |
| Secondary water, cold | 168.01 | 34.1 | 168.01 | 34.3 | 168.01 | 34.3 | 168.01 | 34.1 |
| Stirring 2000 rpm, temp. 29-31° C. | | | | | | | | |
| Secondary starch | 158.68 | 32.2 | 158.68 | 32.4 | 158.68 | 32.4 | 158.68 | 32.2 |
| Stirring 200 sec at 2000 rpm | | | | | | | | |
| Sodium aluminate (Gilunal A) | 2.49 | 0.5 | | | | | 2.49 | 0.5 |
| Stirring 600 sec at 2000 rpm | | | | | | | | |
| Temp. 31-33° C. | 31° C. | | 33° C. | | 31° C. | | 31° C. | |
| Total glue | 492.63 | 100.0 | 489.73 | 100.0 | 490.14 | 100.0 | 492.22 | 100.0 |
| DS % (commercial, only starch calc.) | 34.9 | | 35.1 | | 35.0 | | 34.9 | |
| DS % absolute | 31.5 | | 31.1 | | 31.2 | | 31.4 | |

Example 3

Improving the Properties of a Starch-Containing Adhesive Composition; Effect on Adhesiveness (MFC and Metals)

Example 2 above did show that the combination of MFC and sodium aluminate can improve the properties of a starch-containing adhesive and increase the production speed as well as the adhesiveness. In this example, the effect of MFC in combination with other metals in an oxidation state of II or higher on the glue properties is investigated in the laboratory. Combinations of MFC and sodium aluminate, calcium carbonate, ammonium zirconium carbonate (AZC) were tested in the starch adhesive and compared to a starch adhesive comprising MFC solely. The gelatinization peak viscosity, reflecting the glue-ability and speed of bonding at the inlet of the corrugators heating section, and the water retention of the adhesives were determined. The compositions are shown in Table 6 and were prepared according to a Stein Hall process (procedure given in Table 5).

TABLE 6

Figure 9:
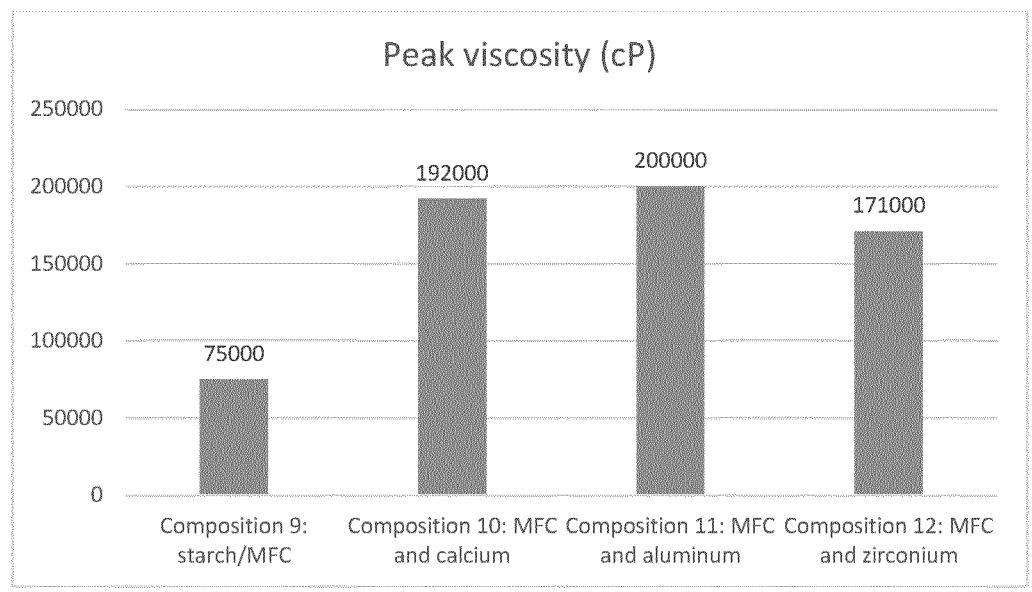
FIG. 9 shows the values of the gelatinization peak viscosity of different starch adhesive compositions based on MFC solely, MFC with calcium, aluminum, and zirconium ions.

Recipes for Laboratory experiments (FIG. 9)

| Ingredient | Composition No. 9 (comparative, starch/ MFC) Mass (g) | Proportion (w-%) | Composition No. 10 (inventive: MFC and calcium) Mass (g) | Proportion (w-%) | Composition No. 11 (inventive: MFC and aluminum) Mass (g) | Proportion (w-%) | Composition No. 12 (inventive: MFC and zirconium) Mass (g) | Proportion (w-%) |
|---|---|---|---|---|---|---|---|---|
| Primary water | 159.6 | 31.9 | 159.6 | 31.9 | 159.6 | 31.8 | 159.6 | 31.8 |
| Primary wheat starch | 15.70 | 3.1 | 15.70 | 3.1 | 15.7 | 3.1 | 15.7 | 3.1 |
| Caustic soda 31% | 3.70 | 0.74 | 3.73 | 0.75 | 3.70 | 0.74 | 3.70 | 0.74 |
| Gilunal A | | | | | 2.50 | 0.50 | | |
| AZC | | | | | | | 1.25 | 0.25 |
| Water | | | | | 50 | 9.95 | 30 | 5.99 |
| Exilva FBX 01-V (10%) | 7.70 | 1.54 | 7.70 | 1.54 | 7.70 | 1.53 | 7.70 | 1.54 |
| Secondary water | 178 | 35.6 | 103 | 20.6 | 128.0 | 25.5 | 148 | 29.5 |
| Secondary starch | 135.1 | 27.0 | 135.1 | 27.0 | 135.1 | 26.9 | 135.1 | 27.0 |
| Calcium carbonate | | | 75 | 15.0 | | | | |
| Total | 499.8 | 100 | 499.8 | 100 | 502.3 | 100 | 501.1 | 100 |
| Starch content | 30.2 | | 30.2 | | 30.0 | | 30.1 | |

The starch used for the laboratory trials was native wheat starch, supplied by Amilina/Roquette. The borax was Fullbor W6364, commercially available from HB Fuller. The sodium aluminate was Gilunal A ($Al_2O_3$ content: 53-55%), commercially available from Kurita. The calcium carbonate was Rollovit 30 from Lhoist ($CaCO_3$ content: 95-97%). The ammonium zirconium carbonate (zirconium content: 15%) was purchased from Sigma Aldrich. The dry solids content (DS) was calculated on commercial base (starch amount in total glue). The pH of the glues was between 11.5-11.8.

FIG. 9 shows the values of the gelatinization peak of the different starch adhesive compositions 9-12. The comparative sample (composition no. 9) exhibits the lowest gelatinization peak value. The three inventive adhesive compositions 10-12 show similar values when compared with each other, but 2.3-2.7 times higher than the comparative composition. The importance of the gelatinization peak viscosity was borne out in several factory trials, where a high gelatinization peak value was reflecting a high production speed in the manufacturing of corrugated boards. In particular, a high gelatinization peak viscosity has shown to be crucial for the high speed production in corrugators under challenging conditions (e.g. unoptimized angles of bars and liners) in the inlet of the heating section. These results clearly demonstrate that the combination of MFC and aluminum and both the combinations of MFC and the metals calcium and zirconium, result in a superior effect for improving the adhesion properties of the starch adhesive.

Moreover, like shown for the inventive composition with MFC and aluminum in Example 2, the water retention value for the combinations of MFC and zirconium, and MFC and calcium, is higher than that of the comparative composition without the respective metal ions.

Without wishing to be bound by theory, it is believed that the higher the oxidation state of the metal, the more can the amount of moles of the metal relative to the weight in kg of the MFC, or relative to the weight in kg of the compound being able to polymerize (here starch), or relative to the weight in kg of the overall adhesive composition, as required to achieve the improved adhesiveness, be reduced.

Example 4

Improving the Properties of a Starch-Containing Adhesive Composition; Effect on Corrugator Speed and Adhesiveness [MFC and Sodium Aluminate (Liquid)]

The inventive compositions comprising MFC and liquid sodium aluminate, compositions No. 13 and 14 in Table 7, were prepared according to the protocol given in Example 2. The starch was native wheat starch, supplied by Amilina/Roquette. The sodium aluminate was AluPurePlus (APP), with $Al_2O_3$ content of 19.9%, commercially available from Alumichem. The primary starch and caustic soda concentrations were adjusted accordingly, to give a viscosity of the adhesives of 35 Lory seconds and a pH of 11.7.

TABLE 7

| Component | Composition No. 13 (inventive) amount (kg) | % | Composition No. 14 (inventive) amount (kg) | % |
|---|---|---|---|---|
| Primary water | 400 | 24.8 | 400 | 25.5 |
| Primary starch | 45 | 2.8 | 47 | 3.0 |
| Water | 70 | 4.3 | 70 | 4.5 |
| Caustic soda (31%) | 11 | 0.7 | 11 | 0.7 |
| Exilva Fbx 01-V | 13 | 0.8 | 12 | 0.8 |
| Secondary water | 540 | 33.5 | 545 | 34.7 |
| Disinfectant | 1 | 0.1 | 1 | 0.1 |
| Secondary starch | 510 | 31.6 | 462 | 29.4 |
| Borax (Fullbor W6364) | 0 | 0.0 | 0 | 0.0 |
| Sodium aluminate (liquid, AluPurePlus) | 22 | 1.4 | 22 | 1.4 |
| Total glue | 1612.0 | 100.0 | 1571.0 | 100.1 |
| DS % (commercial, only starch calc.) | 34.4 | | 32.4 | |
| DS % absolute (dry solids content, "dry matter") | 31.1 | | 29.3 | |

Compositions no. 13 and 14 in Table 7 were used in the production of corrugated boards, according to the protocol given above (Example 2). The performance of composition no. 13 was compared to the performance of composition no. 4 (Table 1), on a double wall EB-flute quality, comprising white liner paper. The same corrugator settings and production speed were used for the both glues. The corrugated boards properties were analyzed and are shown below in Table 8.

TABLE 8

| | EB flute 135WL/100WF/100WF/100WF/135EK | | | | |
|---|---|---|---|---|---|
| Paper combination | Standard | Unit | Composition No. 4 (comparative) | Composition No. 13 (inventive) | % Change |
| Production speed | — | m/min | 154 | 154 | 0.0 |
| $GAP_{db}$-B | — | mm | 0.23 | 0.23 | 0.0 |
| Conditioning | ISO 187 | ° C. | 23 | 23 | 0.0 |
| | | % RH | 50 | 50 | 0.0 |
| Grammage | ISO 536 | g/m² | 652 | 657 | 0.8 |
| Glue consumption | — | g/m² | 27 | 32 | 18.5 |
| Thickness | ISO 3034 | mm | 4.18 | 4.20 | 0.5 |
| Bursting strength | ISO 2759 | kPa | 1301 | 1304 | 0.2 |
| Compression, $ECT_{cd}$ | ISO 3037 | kN/m | 7.8 | 8.0 | 2.6 |
| Torsional stiffness$_{md}$ | GTm34024 | bpi | 17.7 | 20.8 | 17.5 |
| PAT Glue strength$_{db}$-B | Fefco 11 | N/m | 348 | 463 | 33.0 |

The adhesive composition comprising the combination of MFC and aluminum results in an increase in bond strength for the upper double backer (db) of 33%, compared to the MFC and borax composition (Table 8). Furthermore, the inventive MFC and aluminum composition result in an increase in ECT and torsional stiffness of 2.6% and 17.5%, respectively, compared to the comparative composition. When run with the same corrugator settings, the higher dry solids of the inventive adhesive probably contributed to an increase in the calculated glue consumption compared to the MFC and borax composition. The glue consumption was calculated according to the following method and equation: Weight of airdry (constant temperature and humidity conditions) corrugated board−ideal weight of the paper=difference=glue consumption.

The performance of the inventive composition no. 14 with lower dry solids than composition no. 13, and more equal to the comparative composition no. 4, was tested on a double wall BC-quality, with semi-chemical fluting paper. The same corrugator settings and production speed were used for the both glues. The corrugated boards properties were analyzed and are given in Table 9.

TABLE 9

| | BC flute 135TL1/110SC/135TL1/110SC/135TL1 | | | | |
|---|---|---|---|---|---|
| Paper combination | Standard | Unit | Composition No. 4 (comparative) | Composition No. 14 (inventive) | % Change |
| Production speed | — | m/min | 126 | 126 | 0.0 |
| Conditioning | ISO 187 | ° C. | 23 | 23 | 0.0 |
| | | % RH | 50 | 50 | 0.0 |
| Grammage | ISO 536 | g/m$^2$ | 723 | 729 | 0.8 |
| Thickness | ISO 3034 | mm | 6.47 | 6.50 | 0.5 |
| Bursting strength | ISO 2759 | kPa | 1372 | 1375 | 0.2 |
| Compression, ECT$_{cd}$ | ISO 3037 | kN/m | 10.4 | 10.7 | 2.8 |
| Torsional stiffness$_{md}$ | GTm34024 | bpi | 24.4 | 25.8 | 5.4 |
| PAT Glue strength$_{db}$-C | Fefco 11 | N/m | 382 | 411 | 7.1 |
| PAT Glue strength$_{db}$-B | Fefco 11 | N/m | 332 | 381 | 12.9 |

Also on this challenging BC-quality, the adhesive composition comprising the combination of MFC and aluminum gives an increase in bond strength for both the upper and lower double backer (db) of 7.1 and 12.9%, respectively, compared to the MFC and borax composition (Table 9). Furthermore, the inventive MFC and aluminum composition gives an increase in ECT and torsional stiffness of 2.8% and 5.4%, respectively, compared to the comparative composition. Thus, the improved glue ability and bond strength results with the inventive composition no. 13 on the EB-quality, are confirmed for inventive composition no. 14 on the BC-quality.

Starch adhesives with the combination of MFC and liquid sodium aluminate have therefore proven to enable the same production speed on complex and heavy double wall qualities, as the borax containing reference adhesive. Furthermore, the improved boards properties and higher strength of the challenging double backer bonds, demonstrates the better adhesion properties achieved with the inventive adhesives compared to the borax containing reference adhesive.

Example 5

Improving the Properties of a PVA-Containing Adhesive Composition

The compositions shown in Table 10 were prepared according to the following protocol: The reference (comparative composition) is prepared by adding the PVA glue one bag mix (Supermix glue with boric acid, powdered mix commercially available as "Supermix" by Borregaard with a PVA content of around 25%) to cold water under stirring. The mixture is heated to 96° C. and stirred for 30 min. The concentration of boric acid in the final adhesive was 0.5%.

The inventive adhesive with MFC and aluminum sulfate is prepared similarly, first, the MFC is added, then the aluminum sulfate, followed by the water and the Supermix glue without boric acid. The mixture is heated to 96° C. and stirred for 30 min. In the examples, liquid aluminum sulfate (provided by Kemira, Al$^{3+}$ content: 4.2%; Al$_2$O$_3$ content 8.1%) or solid aluminum sulfate hydrate (Al$_2$(SO$_4$)$_3$·xH$_2$O, 7.9-9.4% Al, Sigma Aldrich) were used (Table 10 and Table 12, respectively).

TABLE 10

| | Composition No. 15 (inventive) | | Composition No. 16 (comparative) | |
|---|---|---|---|---|
| Component | amount (kg) | % | amount (kg) | % |
| PVA glue one bag mix (Supermix) without boric acid | 1080 | 26.1 | 0 | 0.0 |
| PVA glue one bag mix (Supermix) with boric acid | 0 | 0.0 | 1100** | 27.4 |
| Exilva P01-L (2%) | 380/7.6* | 9.2/0.2 | 0 | 0.0 |
| Aluminum sulfate (liquid, 4.2% Al$^{3+}$) | 181/7.6* | 4.4/0.2 | 0 | 0.0 |
| Water | 2500 | 60.4 | 2903 | 72.5 |
| Total weight | 4141 | 100.0 | 4003 | 100.0 |
| DS absolute calc. | | 25.4 | | 25.3 |
| pH | | 2.5 | | 4.1 |

*= dry based as MFC or Al.
**= Including 20 kg Boric acid

The adhesive compositions of Table 10 were tested in a large-scale solid board production. Different qualities of paper were tested during the trial and from 4 to 5 papers were glued together. The quality parameters of the solid boards thus produced are summarized in Table 11 below.

TABLE 11

| Parameter | Parameter determined according to: | unit | Composition No. 16 (comp.) | Composition No. 15 (inventive) | Diff. % |
|---|---|---|---|---|---|
| Read | ISO 187 | ° C. | 23 | 23 | |
| Read | ISO 187 | % RH | 50 | 50 | |
| Grammage | ISO 536 | g/m$^2$ | 977 | 970 | −0.8 |
| Thickness | ISO 3034 | mm | 1.33 | 1.30 | −2.6 |
| Density | | kg/m$^3$ | 735 | 749 | 1.9 |
| Bulk | | cm$^3$/g | 1.36 | 1.34 | −1.9 |
| Burst | ISO 2759 | kPa | 1928 | 2158 | 11.9 |
| ECTmd | ISO 3037 | kN/m | 17.0 | 18.9 | 11.2 |
| TScd | GTm34024 | bpi | 5.6 | 5.4 | −3.6 |
| Warp | SUW std | % | 2.4 | 2.0 | −18.8 |
| Water abs (1 h) | GTm34012 | %-weight inc | 11.2 | 5.4 | −51.8 |
| Moisture HM | ISO 287 | % | 11.0 | 9.8 | −11.4 |

As it is evident from Table 11, the inventive adhesive composition leads to a variety of improved effects over a boric acid-containing adhesive composition, such as increased burst strength of 12%, increased ECT (edge wise crush resistance) by 11%, reduced warp by 19% and reduced water adsorption by 52%.

Further, a maximum running speed of 144 m/min could be reached due to the significantly increased adhesiveness, which is in agreement with initial tack measurements shown below.

Also, the boards were flatter than reference boards using a boric acid-containing adhesive composition. Thus, a higher number of boards can then be stacked. Also, the solid boards prepared with the inventive adhesive composition had smoother cut edges, i.e. after cutting, the edges had the appearance of being smoothly sealed.

Furthermore, the adhesive compositions shown in Table 12 were tested for initial tack and water uptake.

The compositions were prepared according to the following general protocol:

Composition No. 20 was prepared by adding the glue powder with boric acid to cold water in a ratio of 1:2.33. The mixture was then stirred at 400 rpm with a dispersion blade to reach a satisfactory dispersion. Then, the composition was heated in an oil bath up to 95° C. and kept there for 10-20 min under continuous stirring. After cooling down the glue was ready to be used.

Composition No. 21 was prepared by first dispersing the MFC in cold water and stirring the mixture at 400 rpm for 5 min with a dispersion blade. Then, the Supermix glue powder (no boric acid) was added and the mixture was stirred for another 10 min. Finally, it was heated to 95° C. and kept at that temperature for 10-20 min while stirring continuously at 400 rpm.

For preparing the inventive adhesive compositions (Compositions 17, 18 and 19), aluminum sulfate was introduced

TABLE 12

| Component | Composition No. 17 (inventive; ALU 0.2 in FIGS. 2, 3 and 4) amount (g) | % | Composition No. 18 (inventive; ALU 0.4 in FIG. 2) amount (g) | % | Composition No. 19 (inventive; ALU 0.6 in FIG. 2) amount (g) | % | Composition No. 20 (comparative, "Ref" in FIGS. 2, 3 and 4) amount (g) | % |
|---|---|---|---|---|---|---|---|---|
| PVA glue one bag mix (Supermix) without boric acid | 142.2 | 28.4 | 141.2 | 28.24 | 140.2 | 28.04 | | |
| PVA glue one bag mix (Supermix) with boric acid | | | | | | | 150 | 30 |
| Exilva P (2%) | 50/1* | 10/0.2 | 50/1* | 10/0.2 | 50/1* | 10/0.2 | | |
| Aluminum sulfate•x H$_2$O (100%) | 1 | 0.2 | 2 | 0.4 | 3 | 0.6 | | |
| Water | 306.8 | 61.36 | 306.8 | 61.36 | 306.8 | 61.36 | 350 | 70 |

| Component | Composition No. 21 (comparative; MFC 0.2 in FIGS. 2, 3 and 4) amount (kg) | % | Composition No. 22 (comparative; ALU 0.2 in FIG. 3) amount (kg) | % |
|---|---|---|---|---|
| PVA glue one bag mix (Supermix) without boric acid | 144.2 | 28.84 | 143.2 | 28.64 |
| Exilva P (2%) | 50/1* | 10/0.2 | | |
| Aluminum sulfate•x H$_2$O (100%) | | | 1 | 0.2 |
| Water | 305.8 | 61.2 | 355.8 | 71.16 | together with the Supermix powder. Otherwise, the same procedure as for preparing Composition No. 21 was used.

Composition No. 22 was prepared by adding the glue powder (no boric acid) and aluminum sulfate to cold water. The mixture was then stirred at 400 rpm with a dispersion blade to reach a satisfactory dispersion. Then, the mixture was heated in an oil bath up to 95° C. and kept there for 10-20 min under continuous stirring. After cooling down the glue was ready to be used.

Figure 1:
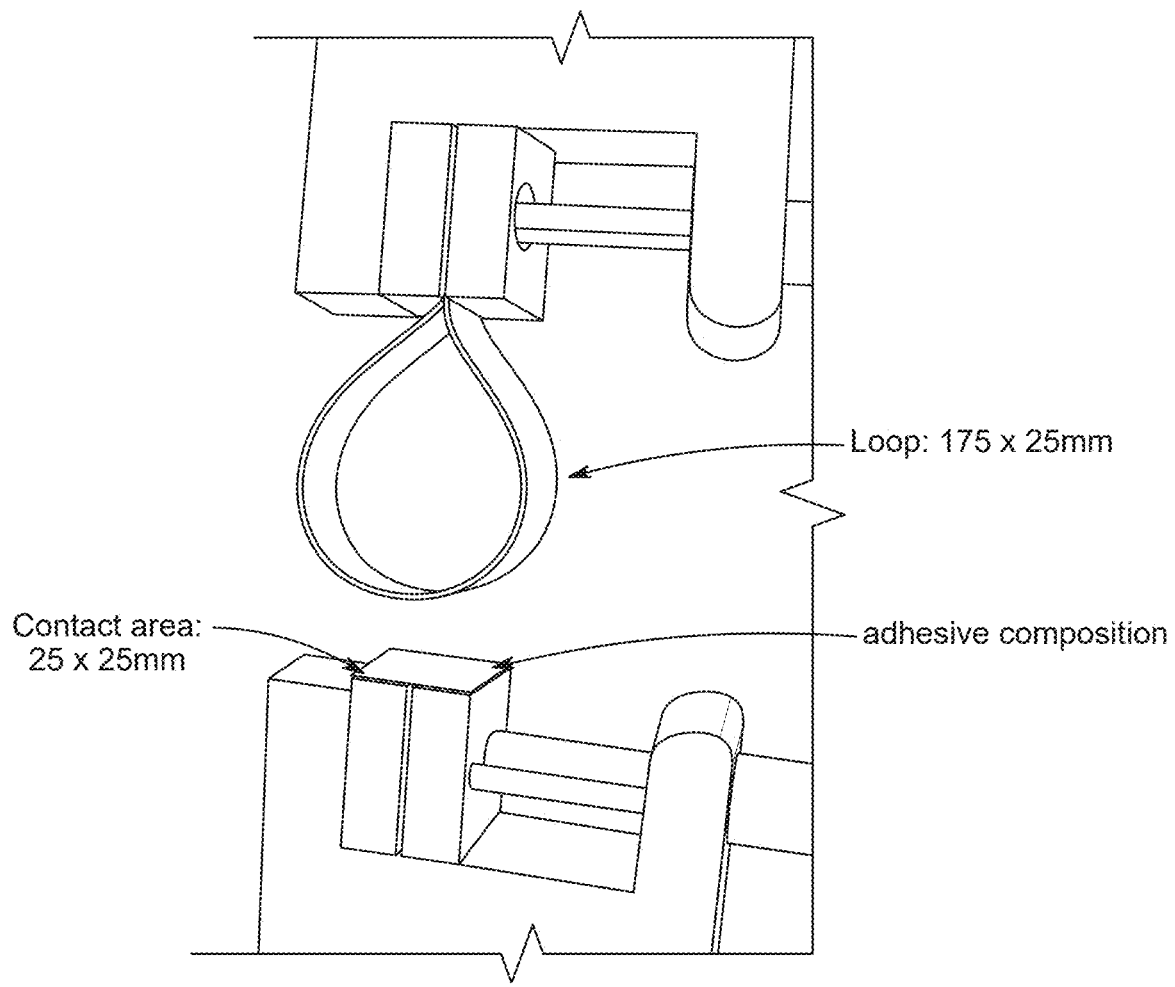
FIG. 1 shows the set-up for determining the initial tack as determined by using a method based on the ASTM D6195 "loop tack" test.

The initial tack was determined by using a method based on the ASTM D6195 Loop tack tests and was carried out on a texture analyzer (TA.XTplus, stable micro systems). Two sets of strips of solid-board were cut, one upper part 175×25 mm and a lower part 90×25 mm. The upper part was formed into a loop and attached in the upper crosshead of the texture analyzer, the lower part was folded in such a way that it could be attached with the lower clamp and a 25×25 mm surface was available for the test. 0.29±0.1 g of glue were applied to the lower part. The complete setup for this measurement method is shown in FIG. 1. The upper part was then approached with a crosshead speed of 10 mm/s to 35 mm from the lower part so that both parts were in full contact. The contact was maintained for 15 s and then the upper part was drawn up with a crosshead speed of 5 mm/s. A 5 kg load cell was used. The force required to tear the pieces apart was recorded and compared as a measure of initial wet tack.

To determine the water uptake, the adhesives were poured onto aluminum pans and dried in an oven with a ventilating fan at 105° C. for 24 h. The dried films were weighed and inserted into glasses with distilled water. To measure the water uptake, the samples were taken out of the water the surfaces dried carefully with a tissue and weighed again. The water uptake was calculated as seen in (equation 1):

$$\text{Water uptake} = (mw - md/md) * 100 \quad (1),$$

wherein mw and md are the mass of the wet and the dry sample respectively. The measurements are first conducted every 20 min for 1 h, then for four hours every hour, and then a final measurement after 24 h, where the values have stabilized.

Figure 2:
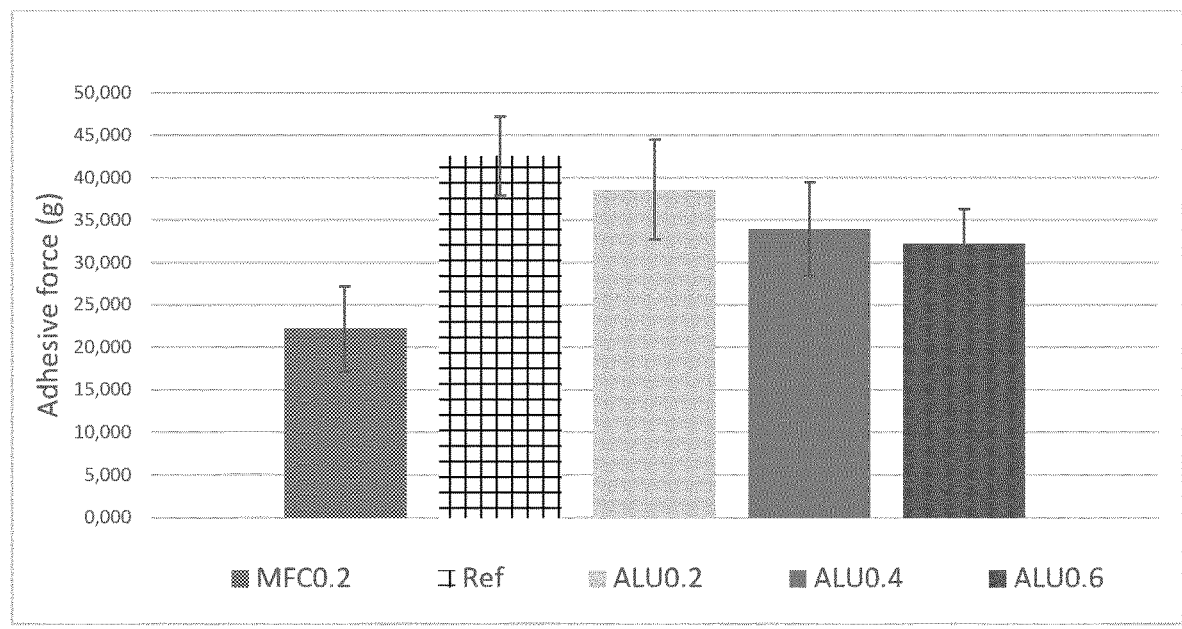
FIGS. 2 and 3 show the initial tack for gluing together two surfaces using adhesive compositions in accordance with the invention and for comparative compositions (FIG. 2, from left to right: compositions 15, 14, 11, 12, 13 as described in the "Examples" Section.
Figure 3:
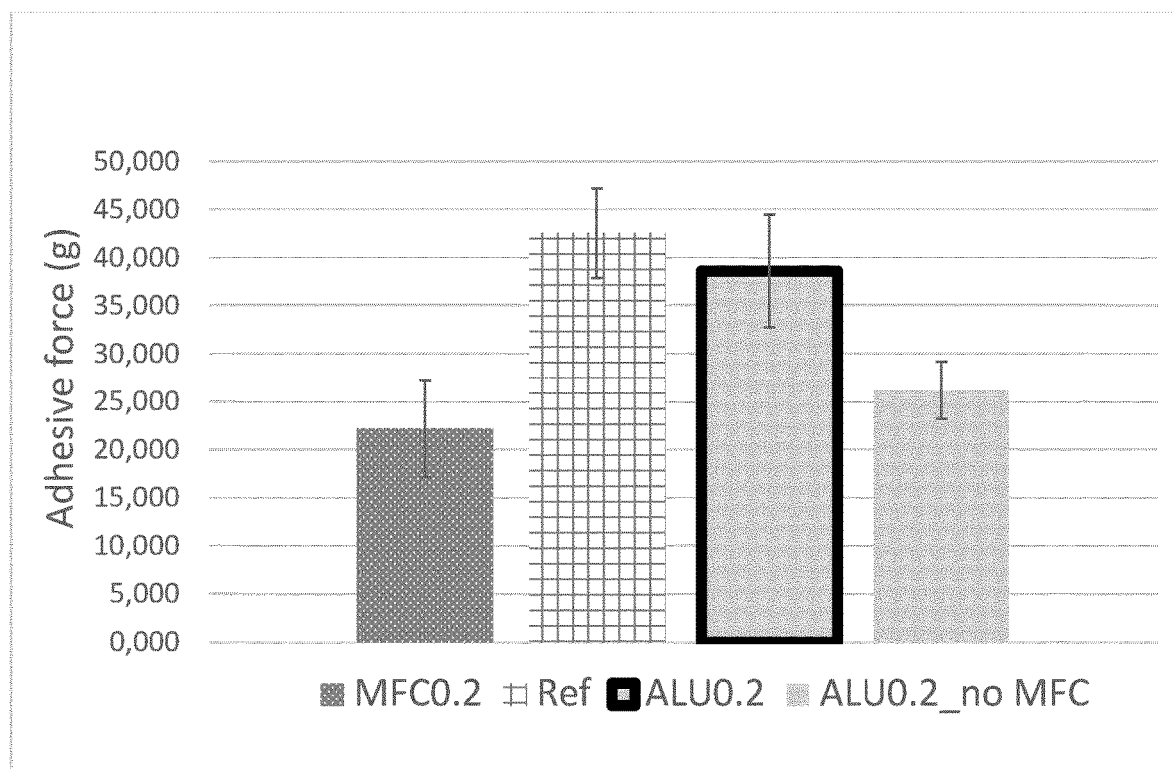

The results for the initial tack are shown in FIGS. 2 and 3.

Figure 4:
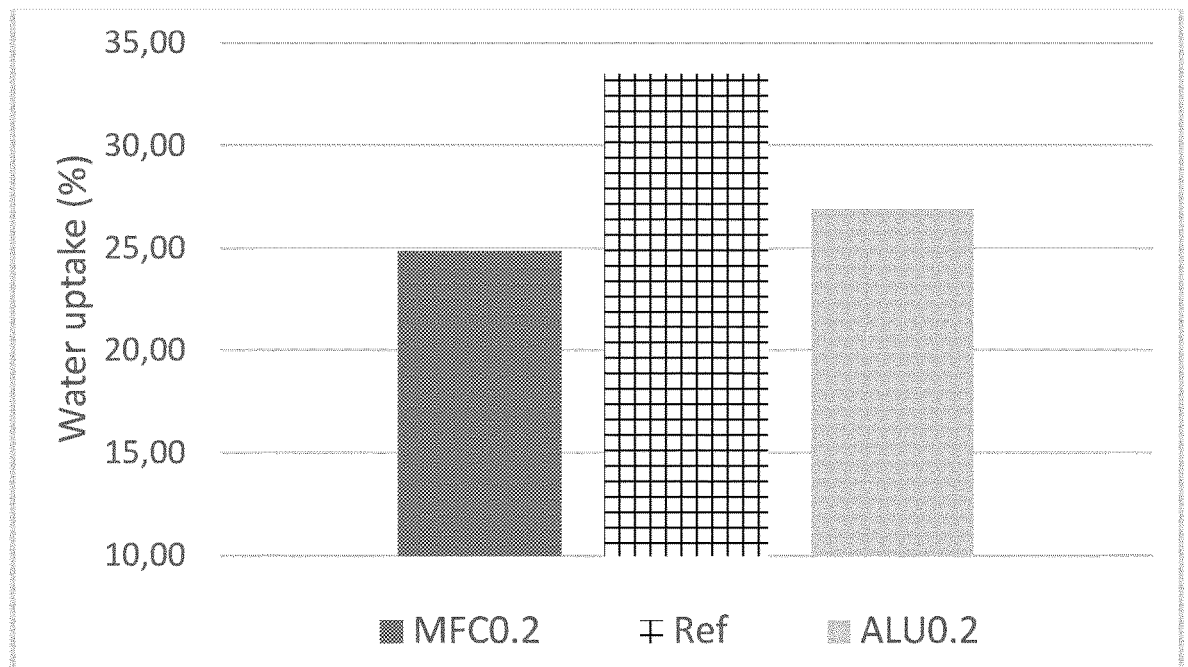
FIG. 4 shows the water uptake of adhesive compositions in accordance with the invention and for comparative compositions (compositions 15, 14, 11 as described in the "Examples" Section).

The results for the water uptake are shown in FIG. 4.

As it can be seen, (reference) composition No. 20 (containing the undesirable boric acid) showed the highest initial tack. Replacing the boric acid by only MFC decreases the initial tack by about 50% (see Composition No. 21) and replacing the boric acid by only aluminum sulfate decreases the initial tack by about 40% (see Composition 22). However, if a combination of MFC and aluminum sulfate is used, the initial tack can be significantly improved relative to using only MFC or only aluminum sulfate. When an amount of 0.2% of MFC and 0.2% of aluminum sulfate (0.1% of anhydrous aluminum sulfate) is used (see Composition 17), the initial tack is similar to that of a boric acid-containing adhesive composition.

Thus, by using a combination of MFC and aluminum sulfate, boric acid can be completely avoided in an adhesive PVA-based composition, without significantly deteriorating the tackiness of the composition.

Further, as it is evident from FIG. 4, a boric acid-containing adhesive composition shows a rather high water uptake, which is generally undesired, because solid-board boxes, where such an adhesive is applied, are often used in moist environments like agriculture or packaging for seafood. However, the water uptake can surprisingly be reduced by adding MFC to the compositions.

Overall, using a combination of MFC and aluminum sulfate allows for the complete removal of boric acid from adhesive compositions while at the same time reducing the water uptake and keeping the tackiness almost constant.

The invention claimed is:
1. Adhesive composition, comprising:
a) microfibrillated cellulose, wherein the microfibrillated cellulose has a Schopper-Riegler (SR) method value of below 95, as determined according to EN ISO 5267-1 (in the version of 1999), or, in the alternative, cannot be reasonably measured in accordance with the SR method, as fibers of the MFC are so small that a large fraction of the fibers simply pass through a screen as defined in the SR method;
b) at least one metal in an oxidation state of II or higher;
c) at least one compound that (a) is capable of polymerizing or has already partly or fully polymerized, and that (b) has at least two groups available for hydrogen bonding that are capable of crosslinking with at least one functional group of the microfibrillated cellulose and/or the at least one metal in an oxidation state of II or higher;
d) at least one solvent,
wherein a relative amount of the at least one metal in an oxidation state of II or higher complies with at least one of the following:
(i) an amount of moles of the at least one metal in an oxidation state of II or higher, relative to a weight, in kg, of an overall adhesive composition, including solvent, is from 0.0005 to 5;
(ii) an amount of moles of the at least one metal in an oxidation state of II or higher, relative to a weight of dry mass of the at least one compound that (a) is capable of polymerizing or has already partly or fully polymerized, and that (b) has at least two groups available for hydrogen bonding that are capable of crosslinking with at least one functional group of the microfibrillated cellulose and/or the at least one metal in an oxidation state of II or higher, in kg, is from 0.002 to 20;
(iii) the at least one metal in an oxidation state of II or higher is present as an oxide, hydroxide or oxyhydroxide, or any mixture thereof, and a weight percentage of said oxide, hydroxide or oxyhydroxide relative to a weight of an overall adhesive composition, including solvent, is from 0.001 to 3.

2. The adhesive composition according to claim 1, wherein the at least one metal in an oxidation state of II or higher comprises Aluminum in an oxidation state of II or higher, Calcium in an oxidation state of II or higher, Zirconium in an oxidation state of II or higher, Magnesium in an oxidation state of II or higher, Zinc in an oxidation state of II or higher, Hafnium in an oxidation state of II or higher or Titanium in an oxidation state of II or higher, or any combination thereof.

3. The adhesive composition according to claim 1, wherein the at least one solvent is a protic solvent.

4. The adhesive composition according to claim 1, wherein the microfibrillated cellulose has at least one length scale, i.e. fibril diameter and/or fibril length, that is reduced vis-a-vis the fiber diameter and/or the fiber length of the cellulose when non-fibrillated.

5. The adhesive composition according to claim 1, wherein an amount of microfibrillated cellulose in said adhesive composition is from 0.001 to 10 wt. % (w/w) based on a total weight of the adhesive composition; or:

wherein a weight ratio of microfibrillated cellulose to the at least one compound that (a) is capable of polymerizing or has already partly or fully polymerized, and that (b) has at least two groups available for hydrogen bonding that are capable of crosslinking with at least one functional group of the microfibrillated cellulose and/or the at least one metal in an oxidation state of II or higher, is from 0.0001 to 0.5.

6. The adhesive composition according to claim 5, wherein the amount of microfibrillated cellulose in said adhesive composition is from 0.01 to 5 wt. % (w/w) based on the total weight of the adhesive composition; or:

wherein the weight ratio of microfibrillated cellulose to the at least one compound that (a) is capable of polymerizing or has already partly or fully polymerized, and that (b) has at least two groups available for hydrogen bonding that are capable of crosslinking with at least one functional group of the microfibrillated cellulose and/or the at least one metal in an oxidation state of II or higher, is from 0.0005 to 0.1.

7. The adhesive composition according to claim 1, wherein the at least one solvent is present in an amount of from 20 to 90 wt. % based on a total weight of the adhesive composition.

8. The adhesive composition according to claim 7, wherein the at least one solvent is present in an amount of from 50 to 80 wt. % based on the total weight of the adhesive composition.

9. The adhesive composition according to claim 1, wherein the composition comprises no or only trace amounts of boron-containing crosslinking agents.

10. The adhesive composition according to claim 1, wherein the at least one compound that (a) is capable of polymerizing, or has already partly or fully polymerized, and that (b) has at least two groups available for hydrogen bonding that are capable of crosslinking with at least one functional group of the microfibrillated cellulose and/or the at least one metal in an oxidation state of II or higher is selected from the group consisting of: at least one starch or starch derivative, at least one polyvinyl alcohol, at least one polyvinyl acetate, at least one polyethylene glycol, at least one polypropylene glycol, at least one polysaccharide, at least one carbohydrate, at least one polypeptide, at least one acrylate, at least one acrylamide, at least one ethylene oxide, at least one propylene oxide, at least one glycol, at least one polyether, at least one polyester, at least one polyol, at least one epoxy resin, at least one polyurethane, at least one polyacrylate, at least one polyurea and at least one carbamide, and any combination thereof.

11. The adhesive composition according to claim 10, wherein the at least one polyacrylate is polymethylmethacrylate (PMMA).

12. The adhesive composition according to claim 1, wherein the at least one metal in an oxidation state of II or higher is present as $Al(OH)_4^-$ and/or is derived from sodium aluminate and wherein the at least one compound that is (a) capable of polymerizing, or has already partly or fully polymerized, and that (b) has at least two groups available for hydrogen bonding that are capable of crosslinking with at least one functional group of the microfibrillated cellulose and/or the at least one metal in an oxidation state of II or higher, is at least one starch or starch derivative.

13. The adhesive composition of claim 12, wherein an amount of microfibrillated cellulose in said adhesive composition is from 0.001 to 10 wt %.

14. The adhesive composition of claim 12, wherein a weight ratio of microfibrillated cellulose to the at least one compound that is (a) capable of polymerizing or has already partly or fully polymerized, and that (b) has at least two groups available for hydrogen bonding that are capable of crosslinking with at least one functional group of the microfibrillated cellulose and/or the at least one metal in an oxidation state of II or higher, is from 0.0001 to 0.5.

15. The adhesive composition according to claim 1, wherein the at least one metal in an oxidation state of II or higher is present as $Al^{3+}$ and/or is derived from aluminum sulfate and wherein the at least one compound that is (a) capable of polymerizing, or has already partly or fully polymerized, and that (b) has at least two groups available for hydrogen bonding that are capable of crosslinking with at least one functional group of the microfibrillated cellulose and/or the at least one metal in an oxidation state of II or higher, is at least one polyvinyl alcohol (PVA).

16. The adhesive composition of claim 15, wherein the amount of microfibrillated cellulose in said PVA-based adhesive composition is from 0.001 to 10 wt %.

17. The adhesive composition of claim 15, wherein the weight ratio of microfibrillated cellulose to the at least one compound that is (a) capable of polymerizing or has already partly or fully polymerized, and that (b) has at least two groups available for hydrogen bonding that are capable of crosslinking with at least one functional group of the microfibrillated cellulose and/or the at least one metal in an oxidation state of II or higher, is from 0.0001 to 0.5.

18. The adhesive composition of claim 1, wherein the relative amount of the at least one metal in an oxidation state of II or higher complies with at least one of the following:

(i) the amount of moles of the at least one metal in an oxidation state of II or higher, relative to the weight, in kg, of the overall adhesive composition, including solvent, is from 0.01 to 0.2;

(ii) the amount of moles of the at least one metal in an oxidation state of II or higher, relative to the weight of the dry mass of the at least one compound that (a) is capable of polymerizing or has already partly or fully polymerized, and that (b) has at least two groups available for hydrogen bonding that are capable of crosslinking with at least one functional group of the microfibrillated cellulose and/or the at least one metal in an oxidation state of II or higher, in kg, is from 0.08 to 2;

(iii) the at least one metal in an oxidation state of II or higher is present as an oxide, hydroxide or oxyhydroxide, or any mixture thereof, and the weight percentage of said oxide, hydroxide or oxyhydroxide relative to the weight of the overall adhesive composition, including solvent, is from 0.1 to 1.

19. Process for making corrugated boards, said process comprising at least the following steps:

a) providing an adhesive composition as defined in claim 1;

b) applying said adhesive composition to at least a part of tips of flutes of a corrugated piece of paper, on at least one side; and c) in a corrugator, applying at least one liner onto said corrugated piece of paper; and d) preparing a single, double, triple or further multiple wall board with said corrugated piece of paper.

20. Corrugated board obtained by a process according to claim 19.

21. A corrugated or solid board comprising an adhesive composition as defined in claim 1.

22. A composition comprising an adhesive composition as defined in claim 1, wherein the composition is a paint composition or size composition.

23. A product comprising an adhesive composition as defined in claim 1, wherein the product is a coating, composite, resin, paste, food thickener or additive, gel, hydrogel, or absorbent.

* * * * *